US008891780B2

(12) United States Patent
Matsuo

(10) Patent No.: US 8,891,780 B2
(45) Date of Patent: Nov. 18, 2014

(54) MICROPHONE ARRAY DEVICE

(75) Inventor: Naoshi Matsuo, Kawasaki (JP)

(73) Assignee: Fujitsu Limited, Kawasaki-shi (JP)

( * ) Notice: Subject to any disclaimer, the term of this patent is extended or adjusted under 35 U.S.C. 154(b) by 852 days.

(21) Appl. No.: 13/107,497

(22) Filed: May 13, 2011

(65) Prior Publication Data

US 2011/0286604 A1 Nov. 24, 2011

(30) Foreign Application Priority Data

May 19, 2010 (JP) ................................. 2010-114897

(51) Int. Cl.
*A61F 11/06* (2006.01)
*H04R 3/00* (2006.01)

(52) U.S. Cl.
CPC ..................................... *H04R 3/005* (2013.01)
USPC ............... 381/71.1; 381/92; 381/97; 381/107

(58) Field of Classification Search
USPC ......... 381/71.1, 122, 92, 56, 58, 94.1, 95, 97, 381/98, 104, 107, 120
See application file for complete search history.

(56) References Cited

U.S. PATENT DOCUMENTS 8,565,445 B2 * 10/2013 Matsuo ........................... 381/92
8,654,992 B2 * 2/2014 Hayakawa ...................... 381/97
2005/0195990 A1 9/2005 Kondo et al.
2007/0274536 A1 11/2007 Matsuo
2008/0170725 A1 * 7/2008 Asada et al. .................. 381/107
2010/0008519 A1 1/2010 Hayakawa et al.
2012/0148067 A1 * 6/2012 Petersen et al. ................. 381/92

FOREIGN PATENT DOCUMENTS

JP 2005-77731 A 3/2005
JP 2005-266797 A 9/2005
JP 2007-174011 A 7/2007
JP 2007-318528 A 12/2007
JP 2010-20165 A 1/2010
JP 2010-124370 A 6/2010

OTHER PUBLICATIONS

Office Action issued on Jan. 14, 2014 in the corresponding Japanese Patent Application No. 2010-114897 (with partial English Translation).

* cited by examiner

*Primary Examiner* — Vivian Chin
*Assistant Examiner* — Friedrich W Fahnert
(74) *Attorney, Agent, or Firm* — Oblon, Spivak, McClelland, Maier & Neustadt, L.L.P.

(57) ABSTRACT

A microphone array device includes a first sound reception unit configured to obtain a first sound signal that is input from a first microphone, a second sound reception unit configured to obtain a second sound signal that is input from a second microphone, a noise state evaluation unit configured to compare the first sound signal and the second sound signal and to obtain an evaluation parameter to evaluate an influence of a non-target sound included in the second sound signal on a target sound included in the first sound signal according to a result of the comparison, a subtraction adjustment unit configured to set a suppression amount for the second sound signal based on the evaluation parameter and to generate a third sound signal; and a subtraction unit configured to generate a signal to be output based on the third sound signal and the first sound signal.

7 Claims, 27 Drawing Sheets

MICROPHONE ARRAY DEVICE

CROSS-REFERENCE TO RELATED APPLICATION

This application is based upon and claims the benefit of priority of the prior Japanese Patent Application No. 2010-114897, filed on May 19, 2010, the entire contents of which are incorporated herein by reference.

FIELD

The embodiments discussed herein relate to a microphone array device.

BACKGROUND

A microphone array device obtains a target sound from a target sound source. The microphone array device uses, for example, a synchronous subtraction method illustrated in FIG. 26 and a method illustrated in FIG. 27. FIGS. 26 and 27 illustrate microphone array devices of related technologies.

A microphone array device 01 in FIG. 26 includes a microphone MIC1 and a microphone MIC2. In FIG. 26, a sound reception direction is set at a left side of the microphone MIC1. Meanwhile, a suppression direction is set at a right side of the microphone MIC2. The sound reception direction includes a target sound source SS. The suppression direction is a direction opposite to the sound reception direction. Both the microphone MIC1 and the microphone MIC2 are non-directional microphones that do not control directivity.

A delay unit 1 delays a sound signal that includes noise obtained by the microphone MIC2 for a certain delay time. A subtraction unit 2 subtracts an output signal of the delay unit 1 from a sound signal that includes a target sound obtained by the microphone MIC1. The microphone array device 01 is configured as a device with directivity that is illustrated by the dotted line in FIG. 26 according to the above-described synchronous subtraction method. In other words, the microphone array device 01 suppresses noise from the suppression direction. The microphone array device 01 may obtain a target sound from a target sound source SS.

A microphone array device 02 in FIG. 27 includes a microphone MIC1 and a microphone MIC2. In FIG. 27, a sound reception range is set at a left side of the microphone MIC1. A shift range and a suppression range are set at a right side of the microphone MIC2. The sound reception range is a range that includes a target sound source SS. The suppression range is a range that is different from the sound reception range. The microphone array device 02 suppresses noise generated from a sound source that is included in the suppression range. The shift range is a range that is set between the sound reception range and the suppression range. Moreover, the shift range is where a degree of suppressing noise is gradually shifted between the sound reception range and the suppression range.

An FFT3*a* applies Fast Fourier Transform (FFT) to convert a sound signal obtained by the microphone MIC1 into a complex spectrum IN1(*f*) on a frequency axis. Likewise, an FFT3*b* applies Fast Fourier Transform (FFT) to convert a sound signal obtained by the microphone MIC2 into a complex spectrum IN2(*f*) on a frequency axis. A phase spectrum difference calculation unit 4 calculates a phase spectrum difference DIFF(f) between the sound signal obtained by the microphone MIC1 and the sound signal obtained by the microphone MIC2 based on the complex spectrum IN1(*f*) and the complex spectrum IN2(*f*). The microphone array device 02 may identify a range where a sound source is included for each frequency by the phase spectrum difference DIFF(f). A gain calculation unit 5 calculates a noise suppression gain G(f) based on the identified range of the sound source. The noise suppression gain G(f) is a variable to determine an input and output ratio. The microphone array device 02 determines how much noise is suppressed by adjusting the noise suppression gain G(f). A noise suppression unit 6 calculates an output OUT(f) in which noise is suppressed based on the complex spectrum IN1(*f*) and the noise suppression gain G(f). An IFFT7 applies reverse FFT to the output OUT(f) to obtain an output. The microphone array device 02 may obtain a target sound from the target sound source SS while suppressing noise.

The above-described related technology is discussed, for example, in Japanese Laid-open Patent Publication No. 2007-318528.

SUMMARY

According to an aspect of the invention, a microphone array device includes a first sound reception unit configured to obtain a first sound signal that is input from a first microphone, a second sound reception unit configured to obtain a second sound signal that is input from a second microphone different from the first microphone, a noise state evaluation unit configured to compare the first sound signal and the second sound signal and to obtain an evaluation parameter to evaluate an influence of a non-target sound included in the second sound signal on a target sound included in the first sound signal according to a result of the comparison, a subtraction adjustment unit configured to set a suppression amount for the second sound signal based on the evaluation parameter and to generate a third sound signal based on the second sound signal and the suppression amount; and a subtraction unit configured to generate a signal to be output based on the third sound signal and the first sound signal.

The object and advantages of the invention will be realized and attained by means of the elements and combinations particularly pointed out in the claims.

It is to be understood that both the foregoing general description and the following detailed description are exemplary and explanatory and are not restrictive of the invention, as claimed.

DESCRIPTION OF EMBODIMENTS

Figure 26:
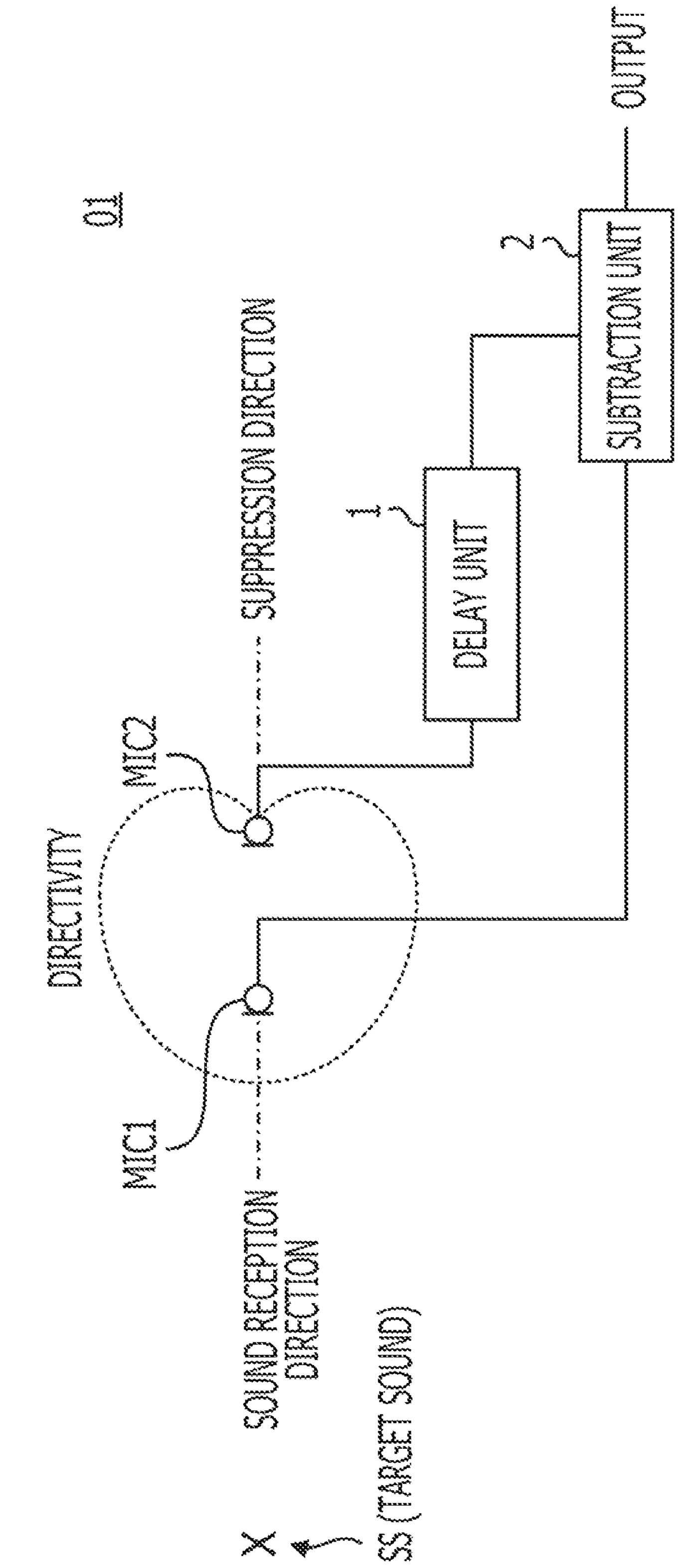
FIG. 26 RELATED ART
FIG. 26 illustrates a microphone array device of related art.

According to the above-described synchronous subtraction method in FIG. 26, a subtraction unit 2 subtracts an output of a delay unit 1 from a sound signal that includes a target sound in order to suppress noise. Thus, a spectrum of the sound signal that includes the target sound is distorted, and there may be an influence, for example, quality of the target sound that is eventually output may be changed.

Moreover, the microphone array device may erroneously recognize a target sound source SS is present at a suppression direction even when the target sound source SS is present at a sound reception direction. Such erroneous recognition may be caused due to fluctuation of an incoming direction of a sound due to a movement of, for example, a speaker who is a target sound source SS, reflection from a wall, and a surrounding environment such as an air flow. In this case, the microphone array device assumes a target sound that comes from the suppression direction as noise even though the target sound source SS is actually present at the sound reception direction and performs the synchronous subtraction as described above. The above-described erroneous recognition is also results in distortion of a spectrum of the sound signal that includes the target sound that is output from the subtraction unit 2 and there may be an influence, for example, quality of the target sound that is eventually output may be changed.

Figure 27:
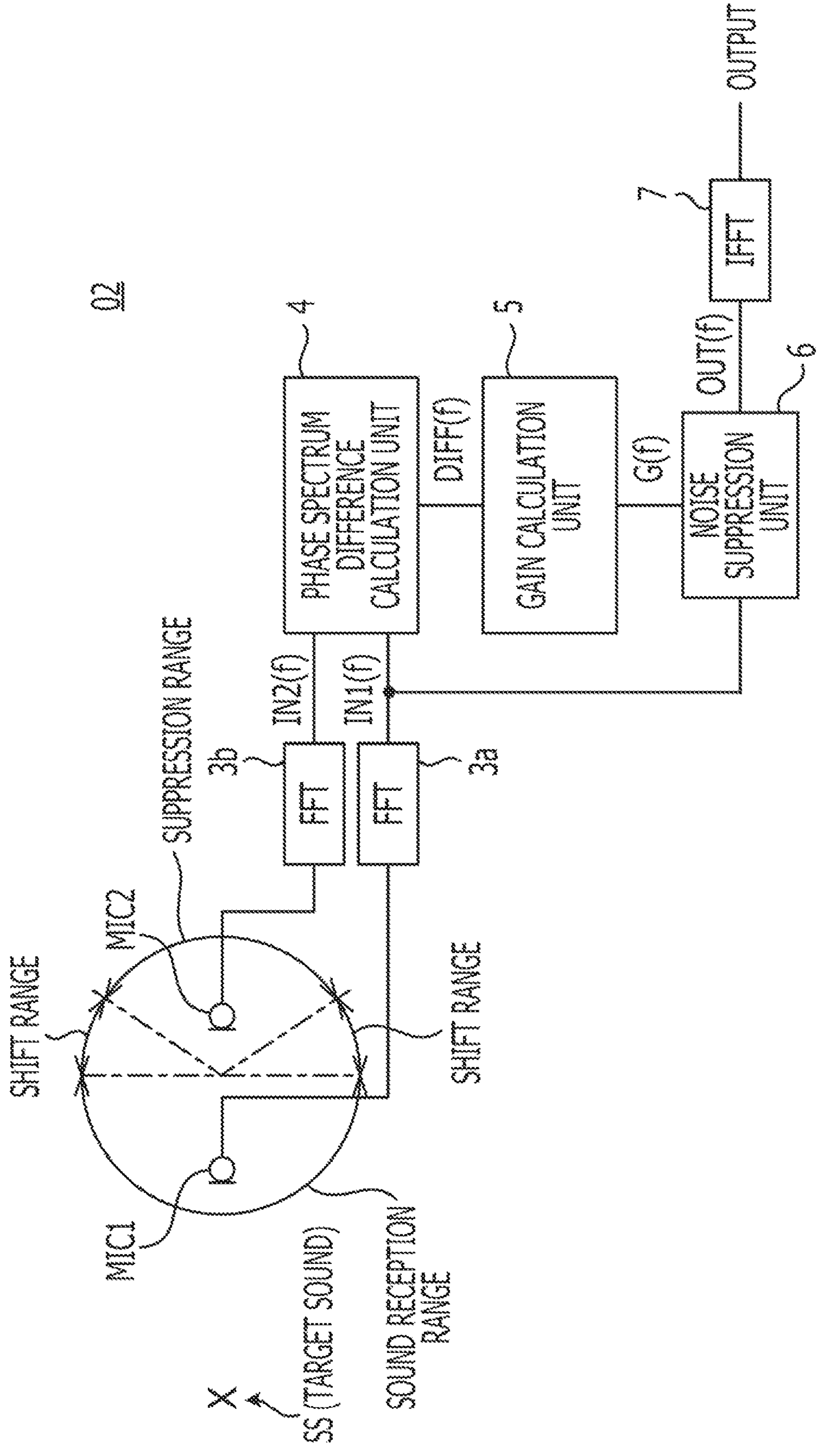
FIG. 27 RELATED ART
FIG. 27 illustrates a microphone array device of related art.

Similar phenomenon is caused in the case of FIG. 27 as well. For example, the microphone array device may erroneously recognize that the target sound source SS is in the shift range and the suppression range due to sound fluctuation by surrounding environment regardless that the target sound source SS is actually present in the sound reception range. In this case, the target sound that comes from the shift range and the suppression range is assumed to be noise and the target sound is suppressed through processing by the phase spectrum difference calculation unit 4, the gain calculation unit 5, and the noise suppression unit 6. Thus a spectrum of the sound signal that includes the target sound that is output from an IFFT7 may be distorted, and there may be an influence, for example, quality of the target sound may be changed.

Furthermore, when a target sound from a target sound source SS is received, for example, by a mobile phone, the sound reception direction and the sound reception range may be changed depending on how the mobile phone is held by the user. In this case, the microphone array device assumes the target sound as noise when the target sound is received from the suppression direction or the suppression range, and the shift range. As a result, the target sound is distorted.

Suppressing noise using, for example, the above-described synchronous subtraction method in FIG. 26 and the method illustrated in FIG. 27 is required. Moreover, it is unavoidable that as described above, the target sound source SS is erroneously recognized to be present in a different position due to, for example, surrounding environment, and thereby assumed to be noise and suppressed. Furthermore, it is also unavoidable that the sound reception direction and the sound reception range are changed due to a movement of a device. However, suppressing distortion of the target sound and improving sound quality are needed.

Hence, embodiments disclosed herein provide a technology to suppress distortion of a target sound while suppressing noise.

According to an embodiment described below, processing is performed using sound signals obtained by two microphones among a plurality of microphones. Out of the two microphones, one microphone mainly obtains a sound that includes a target sound from a sound reception direction or a sound reception range. The other microphone mainly obtains a sound that includes noise from a suppression direction, a suppression range, or a shift range. In other words, the microphone positioned in the sound reception direction or the sound reception range obtains a non-suppression sound signal as a sound signal from a non-suppression direction that is other than the suppression direction, the suppression range, or the shift range. On the other hand, the microphone positioned in the suppression direction, the suppression range, or the shift range obtains a suppression sound signal. The non-suppression sound signal includes a target sound, while the suppression sound signal includes a non-target sound. The non-target sound differs from the target sound, and for example, is noise.

A microphone array device according to the embodiment described below suppresses distortion of a target sound while suppressing noise. The microphone array device obtains an evaluation parameter to evaluate an influence of a non-target sound on the target sound based on a result of comparison between a non-suppression sound signal from the non-suppression direction and a suppression sound signal from the suppression direction. The microphone array device controls a suppression amount of the non-target sound based on the evaluation parameter. Furthermore, the microphone array device controls directivity of the microphones.

The evaluation parameter includes a parameter that indicates a state of noise such as a noise level and a noise level change. Moreover, the evaluation parameter includes a parameter that indicates a direction of a target sound source by an evaluation result of a level of each sound signal. Hereinafter, examples of methods to suppress noise based on an evaluation parameter that indicates a state of noise will be described by referring to the first to third embodiments. Moreover, one example of a method to determine a sound reception direction based on an evaluation parameter that indicates a target sound direction will be described by a fourth embodiment.

First Embodiment

According to the first embodiment, a microphone array device obtains a state of noise by processing sound signals obtained by two microphones on a time axis, and suppresses noise by synchronous subtraction processing based on the state of noise.

(1) Hardware Configuration

Figure 1:
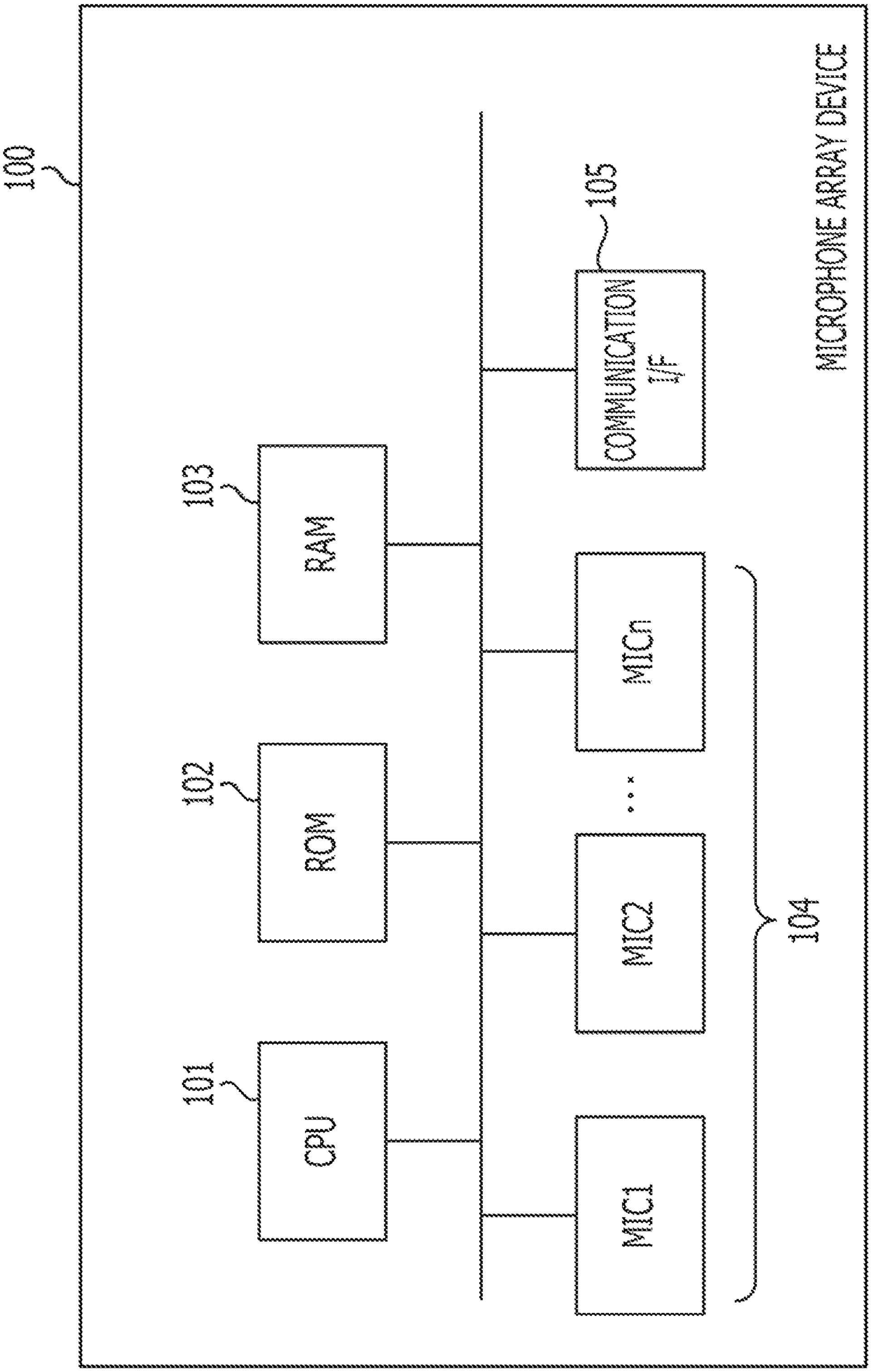
FIG. 1 is a block diagram illustrating a hardware configuration of a microphone array device according to a first embodiment.

FIG. 1 is one example of a block diagram illustrating a hardware configuration of a microphone array device according to the first embodiment. A microphone array device 100 includes a Central Processing Unit (CPU) 101, a Read Only Memory (ROM) 102, a Random Access Memory (RAM) 103, a microphone array device 104, and a communication interface (I/F) 105.

The microphone array device 104 includes at least two microphones, and here includes microphones MIC1, MIC2, . . . MICn (n is an integer 3 or more). Controlling directivity of the microphone array device 104 allows to receive mainly a desired target sound from a sound reception direction, thereby allows to suppress noise.

The ROM 102 stores various control programs for various controls, which will be described later, performed by the microphone array device 100. The various programs include, for example, a program to obtain a state of noise and a program to suppress noise, which will be described later. The ROM 102 stores various values such as a value A1 and a value A2 as thresholds, and constants or coefficients such as $\alpha$, $\beta$, and $\tau$, which will be described later. Moreover, the ROM 102 stores relationships that are set, for example, between a noise level L(f) and a relative value of the level(f), and that between noise level change S(f) and Rate(f), which will be described later.

The RAM 103 temporarily stores various control programs in the ROM 102 and sound signals obtained by the microphone array device 104. The RAM 103 temporarily stores information such as various flags according to execution of various control programs.

The CPU 101 expands various programs stored in the ROM 102 into the RAM 103 and performs various controls.

A communication I/F 105 connects the microphone array device 100 to an external network etc. based on control by the CPU 101. For example, the microphone array device 100 is connected to a sound recognition device through the communication I/F 105 and outputs a sound signal processed by the microphone array device 100 to the sound recognition device.

(2) Functional Configuration

Figure 2:
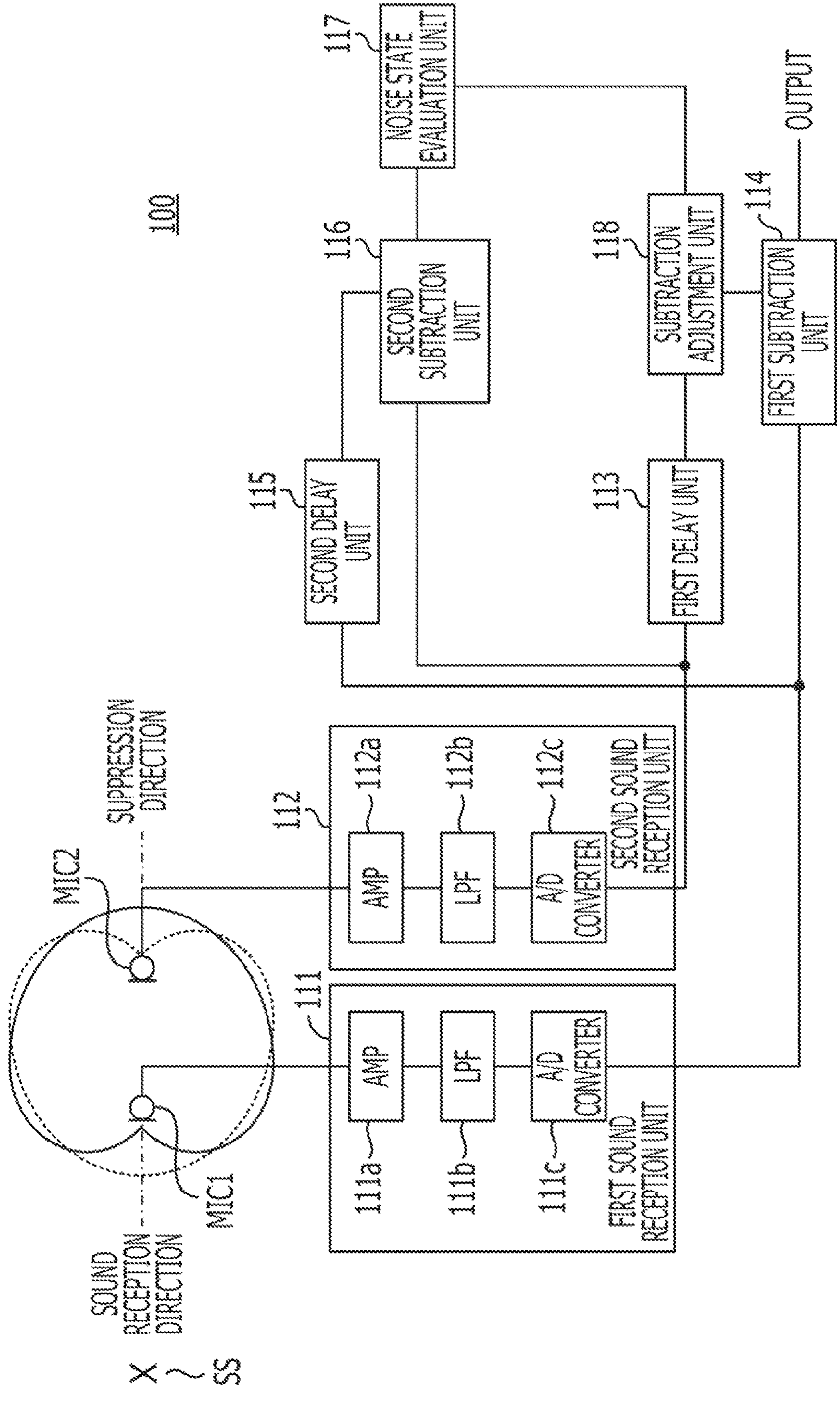
FIG. 2 is a block diagram illustrating a functional configuration of the microphone array device according to the first embodiment.

FIG. 2 is a block diagram illustrating a functional configuration of the microphone array device according to the first embodiment. FIG. 2 illustrates a microphone MIC1 and a microphone MIC2 among a microphone array 104 of the microphone array device 100. Here, the microphone MIC1 and the microphone MIC2 are directional microphones, and disposed along a substantially straight line.

In FIG. 2, the target sound source SS is positioned at the left side of the microphone MIC1 while the sound reception direction is set at the left side of the microphone MIC1. Moreover, the suppression direction is set at the right side of the microphone MIC2. Here, the target sound source SS is a sound source where a target sound is generated. The sound reception direction is a direction where the target sound source SS is included. Meanwhile, the suppression direction is a direction opposite to, for example, the sound reception direction. The suppression direction is set to, for example, a direction that is 180 degrees different from the reception sound direction. Furthermore, according to the embodiment, the sound that comes from the suppression direction is assumed to be noise. The sound reception direction and the suppression direction may be set by a user through a user input acceptance unit (not illustrated) of the microphone array device 100. Alternatively, a direction identification unit (not illustrated) of the microphone array device 100 may identify a target sound source SS. The sound reception direction and the suppression direction may be set based on the identified target sound source SS.

A distance d between the microphone MIC1 and the microphone MIC2 are set by the following expression (1) so as to satisfy the sampling theorem.

$$\text{Microphone distance } d = \text{speed of sound } c/\text{sampling frequency } fs \quad (1)$$

Processing by functional units of the microphone array device 100 is executed in collaboration with the CPU 101, the ROM 102, the RAM 103, and the microphone array 104 and so on.

The functional units of the microphone array device 100 include, for example, a first sound reception unit 111, a second sound reception unit 112, a first delay unit 113, a first subtraction unit 114, a second delay unit 115, a second subtraction unit 116, a noise state evaluation unit 117, and a subtraction adjustment unit 118. Each of the functional units will be described below.

(2-1) The First Sound Reception Unit and the Second Sound Reception Unit

The microphone MIC1 obtains a sound that includes a target sound. The microphone MIC1 converts the obtained sound into an analog signal and inputs the analog signal to the first sound reception unit 111. The first sound reception unit 111 includes an Amplifier (AMP) 111*a*, a Low Pass Filter (LPF) 111*b*, and an analog to digital (A/D) converter 111*c*. The first sound reception unit 111 generates a sound signal by processing the sound including the target sound that is input from the microphone MIC1.

The AMP111*a* amplifies the analog signal that is input from the microphone MIC1 and inputs the amplified signal to the LFP 111*b*.

The LFP111*b*, which is a low pass filter, applies a low-pass filter to an output of the AMP111*a*, for example, by a cut-off frequency fc. Here, typically the low pass filter is used. However, the low pass filter may be used together with a band pass filter or a high frequency pass filter.

The A/D converter 111*c* takes in an output of the LFP 111*b* at a sampling frequency fs (fs>2fc), and converts the output of the LFP 111*b* into a digital signal. The A/D converter 111*c* outputs a sound signal in1($t_i$) on a time axis.

The microphone MIC2 obtains a sound including noise, converts the sound into an analog signal, and inputs to the second sound reception unit 112. The second sound reception unit 112 includes an AMP112*a*, an LPF112*b*, and an A/D converter 112*c*. The second sound reception unit 112 processes the sound including noise that is input from the microphone MIC2 to generate a sound signal. Processing by the AMP112*a*, the LPF112*b*, and the A/D converter 112*c* is substantially the same as that of the AMP111*a*, the LPF111*b*, and the A/D converter 111*c*. The second sound reception unit 112 outputs a sound signal in2($t_i$) as a digital signal on a time axis.

(2-2) The Second Delay Unit and the Second Subtraction Unit

The second delay unit 115 and the second subtraction unit 116 control directivity of the microphone array that is made up of the microphone MIC1 and the microphone MIC2. For example, the second delay unit 115 and the second subtraction unit 116 control directivity so that a sound from a direction other than the sound reception direction, in other words, a sound from the suppression direction is taken in. One example of directivity of a sound signal that is output from the second delay unit 115 and the second subtraction unit 116 is indicated in FIG. 2 by the solid line as "opposite directivity." The microphone array device 100 obtains a sound including noise that comes from the suppression direction.

Processing by the second delay unit 115 and the second subtraction unit 116 is applied to a direction opposite to processing by the first delay unit 113 and the first subtraction unit 114. Processing by the first delay unit 113 and the first subtraction unit 114 controls directivity so that a sound from the sound reception direction is taken in as will be described later. In other words, directivity controlled by the first delay unit 113 and the first subtraction unit 114 is indicated by the dashed line in FIG. 2 as "positive directivity." Here, a difference between the sound reception direction and the suppression direction is 180 degree, and "positive directivity" and "opposite directivity" are left and right symmetric.

The second delay unit 115 receives a sound signal in1($t_i$) that includes a target sound from the first sound reception unit 111. The second delay unit 115 generates a sound signal that is obtained by delaying the sound signal in1($t_i$) for a certain period Ta. The sound signal delayed by the second delay unit 115 is represented by the in1($t_i$−1). The certain period Ta here is, for example, time dependent on a microphone distance d between the microphone MIC1 and the microphone MIC2. When the microphone distance d is set as in the above expression (1), the certain period Ta is defined by the expression below:

$$\text{signal sampling interval}=1/\text{sampling frequency } fs$$

The $t_i$ is time when a sound signal is taken in the microphone and the subscript $_i$ of t is a sampling number of each sound signal when the sound is taken in with a sampling frequency fs. The $t_i$ is an integer of one or more.

The second subtraction unit 116 receives a sound signal in2($t_i$) that includes noise from the second sound reception unit 112 and subtracts the sound signal in1($t_i$−1) after applying the delay from the sound signal in2($t_i$). In other words, the second subtraction unit 116 calculates a noise signal N ($t_i$) by the expression (2) below.

$$\text{noise signal } N(t_i)=\text{sound signal in2}(t_i)-\text{sound signal in1}(t_i-1) \qquad (2)$$

The above described processing sets directivity of the noise signal N ($t_i$) that is output from the second subtraction unit 116 to "opposite directivity." In other words, a sound from a direction other than the sound reception direction that includes a target sound source SS is mainly taken in while suppressing a sound signal that includes a target sound from the sound reception direction. As a result, the second subtraction unit 116 outputs a noise signal N ($t_i$) in which noise from the suppression direction is emphasized. The microphone array device 100 according to the embodiment may recognize a state of noise by the noise signal N ($t_i$).

(2-3) Noise State Evaluation Unit

The noise state evaluation unit 117 evaluates a state of noise based on the noise signal N ($t_i$) that is an output of the second subtraction unit 116. The state of noise includes, for example, a noise level and a noise level change. The noise level is an indicator that represents a magnitude of noise. The noise level change is an indicator that represents whether temporal noise level change is large or small. When a noise level change is small, steadiness of the noise is high. In other words, non-steadiness of noise is low. Conversely, when noise level change is large, steadiness of noise is low. In other words, non-steadiness of noise is high. The noise level and noise level change are represented, for example, by the expressions (3) and (4) below.

$$\text{noise level } L(t_i)=10\log_{10}(N(t_i)^2) \qquad (3)$$

$$\text{noise level change } S(t_i)=\text{noise level } L(t_i)/\text{average value of noise level before time } t_i \qquad (4)$$

The noise state evaluation unit 117 may obtain a combined value LS ($t_i$) as a function in which both the noise level L($t_i$) and the noise level change S($t_i$) are variables.

(2-4) Subtraction Adjustment Unit

The subtraction adjustment unit 118 sets a gain g($t_i$) for adjusting a suppression amount of noise on a time axis according to a state of noise. Adjusting the gain g($t_i$) adjusts an input and output ratio of the subtraction adjustment unit 118. The subtraction adjustment unit 118 adjusts a subtraction amount when the first subtraction unit 114 subtracts the sound signal in2($t_{i-1}$) from the sound signal in1($t_i$). As a result, a suppression amount of noise included in a sound that is obtained by the microphone MIC1 is adjusted. The gain g($t_i$) is 0 or more and 1.0 or less. Moreover, the gain g($t_i$) may be updated at each sampling of a sound signal. Alternatively, the gain $g(t_i)$ may be updated in units of a plurality of samplings.

For example, the subtraction adjustment unit 118 makes the gain $g(t_i)$ closer to 1.0 as the noise level $L(t_i)$ becomes higher. The subtraction adjustment unit 118 makes the gain $g(t_i)$ closer to 1.0 as a noise level change $L(t_i)$ is larger and steadiness is lower. The subtraction adjustment unit 118 makes the gain $g(t_i)$ closer to 0 as a noise level change $L(t_i)$ is smaller and steadiness is higher. Specific examples will be described below.

Setting Gain $g(t_i)$ According to Noise Level $L(t_i)$

Figure 3:
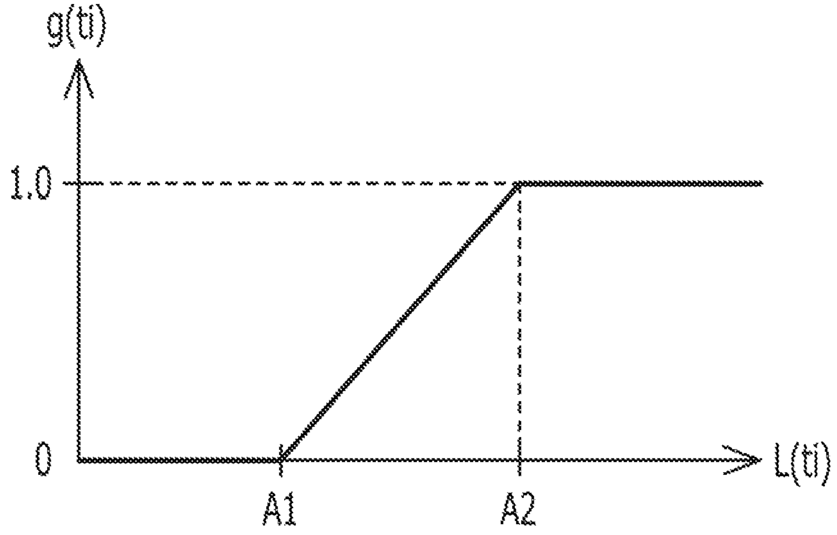
FIG. 3 illustrates one example of a relationship between a noise level L(ti) and a gain $g(t_i)$.

FIG. 3 illustrates one example of a relationship between a noise level $L(t_i)$ and a gain $g(t_i)$. The values A1 and A2 are thresholds.

(a1) Noise Level $L(t_i)$<value A1: gain $g(t_i)=0$

For example, when the noise level $L(t_i)$ is smaller than the value A1, the subtraction adjustment unit 118 determines the noise level $L(t_i)$ is low and sets the gain $g(t_i)$ to 0.

(a2) Noise Level $L(t_i)$>value A2: gain $g(t_i)=1.0$

Conversely, when the noise level $L(t_i)$ is greater than the value A2, the subtraction adjustment unit 118 determines the noise level $L(t_i)$ is high and sets the gain $g(t_i)$ to 1.0.

(a3) Value A1≤Noise Level $L(t_i)$≤Value A2

When the noise level $L(t_i)$ is the value A1 or more and the value A2 or less, for example, the gain $g(t_i)$ is set by a simple weighted average indicated by the following expression (5). The simple weighted average is one example and an arithmetic average, a quadratic weighted average, and a cubic weighted average may be used as well.

$$\text{gain } g(t_i)=(\text{noise level } L(t_i)-A1)/(A2-A1) \quad (5)$$

(b) Setting Gain $g(t_i)$ According to a Noise Level Change $S(t_i)$

Figure 4:
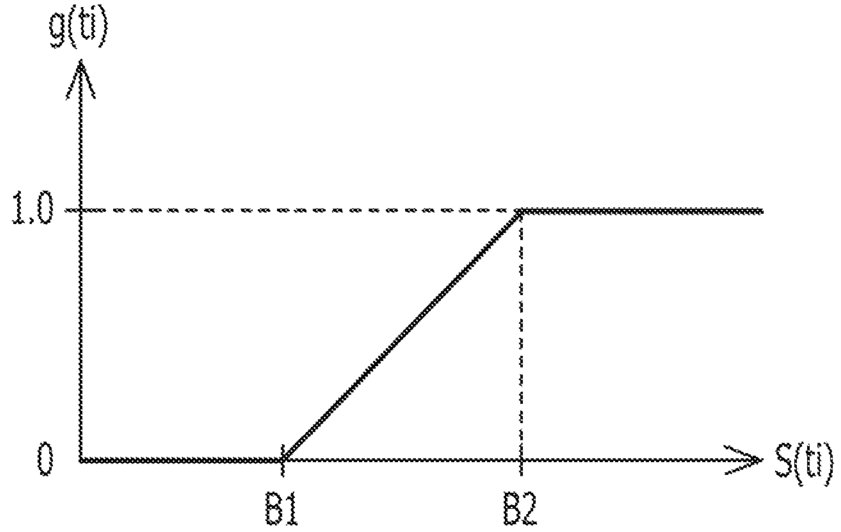
FIG. 4 illustrates one example of a relationship between a noise level change S(ti) and a gain g(ti)

FIG. 4 illustrates one example of a relationship between a noise level change $S(t_i)$ and a gain $g(t_i)$. The values B1 and B2 are thresholds.

(b1) Noise Level Change $S(t_i)$<Value B1: Gain $g(t_i)=0$

For example, when a noise level change $S(t_i)$ is smaller than the value B1, the subtraction adjustment unit 118 determines the noise level change is small and steadiness is high, and sets the gain $g(t_i)$ to 0.

(b2) Noise Level Change $S(t_i)$>Value B2: Gain $g(t_i)=1.0$

Conversely, when a noise level change $S(t_i)$ is greater than the value B2, the subtraction adjustment unit 118 determines the noise level change is large and steadiness is low, and sets the gain $g(t_i)$ to 1.0.

(b3) Value B1≤Noise Level Change $S(t_i)$≤Value B2

When the noise level change $S(t_i)$ is the value B1 or more and the value B2 or less, the subtraction adjustment unit 118 sets the gain $g(t_i)$ by a simple weighted average by the following expression (6). The simple weighted average is one example, and an arithmetic average, a quadratic weighted average, and a cubic weighted average may be used as well.

$$\text{gain } g(t_i)=(\text{noise level change } S(t_i)-B1)/(B2-B1) \quad (6)$$

(c) Setting Gain $g(t_i)$ According to Noise Level $L(t_i)$ and Noise Level Change S(ti)

The subtraction adjustment unit 118 may set a gain $g(t_i)$ based on either one of the noise level $L(t_i)$ or the noise level change $S(t_i)$, or both of the noise level $L(t_i)$ and the noise level change $S(t_i)$.

For example, when noise level $L(t_i)$<value A1, and/or noise level change $S(t_i)$<value B1, the subtraction adjustment unit 118 sets the gain $g(t_i)$ to 0. Moreover, when noise level $L(t_i)$ >value A2, and/or noise level change $s(t_i)$>value B2, the subtraction adjustment unit 118 sets the gain $g(t_i)$ to 1.0

When one of the following conditions is satisfied: value A1≤noise level $L(t_i)$≤value A2, and/or, value B1≤noise level change $S(t_i)$≤value B2, the gain $g(t_i)$ may be set as follows. The subtraction adjustment unit 118 sets the gain $g(t_i)$ based on the above expression (5) when a state of noise that satisfies the condition is the noise level $L(t_i)$. Moreover, the subtraction adjustment unit 118 sets the gain $g(t_i)$ based on the above expression (6) when a state of noise that satisfies the condition is the noise level $S(t_i)$. Meanwhile, the subtraction adjustment unit 118 sets the gain $g(t_i)$ based on the above expression (5) or expression (6) when both of the conditions are satisfied.

Other than the above described settings, the subtraction adjustment unit 118 may set the gain $g(t_i)$ according to a combined value $LS(t_i)$. Accordingly, noise suppression processing that takes account of the noise level $L(t_i)$ and noise level change $S(t_i)$ may be performed.

The subtraction adjustment unit 118 receives a sound signal in2($t_{i-1}$) from a first delay unit 113, which will be described later. The subtraction adjustment unit 118 multiplies the sound signal in2($t_i$) by the gain $g(t_i)$ and outputs the multiplication result to the first subtraction unit 114.

(2-5) The First Delay Unit and the First Subtraction Unit

The first delay unit 113 and the first subtraction unit 114 control directivity so that a sound mainly from the sound reception direction is taken in. The directivity is indicated by the dashed line in FIG. 2 as "positive directivity." Accordingly, the microphone array mainly obtains a sound including a target sound that comes from the sound reception direction.

The first delay unit 113 takes in a sound signal in2($t_i$) including noise from the second sound reception unit 112. The first delay unit 113 generates a sound signal, for example, in2($t_{i-1}$) that is obtained by delaying the sound signal in2($t_i$) for a certain period Ta. The first delay unit 113 outputs the in2($t_{i-1}$) to the subtraction adjustment unit 118.

The first subtraction unit 114 receives a sound signal in1($t_i$) including a target sound from the first sound reception unit 111. The first subtraction unit 114 receives a result of multiplying the sound signal in2($t_{i-1}$) by the gain $g(t_i)$ from the subtraction adjustment unit 118. The first subtraction unit 114 subtracts the multiplication result from the sound signal in1 ($t_i$) and outputs a target sound signal OUT ($t_i$) as represented by the expression (7) below.

$$\text{target sound signal OUT}(t_i)=\text{sound signal in1}(t_i)-\text{sound signal in2}(t_{i-1})\times\text{gain } g(t_i) \quad (7)$$

Through the above described processing, the target sound signal OUT ($t_i$) that is output from the first subtraction unit 114 indicates a directivity that takes in a sound from the sound reception direction as indicated by the dashed line in FIG. 2. In other words, a sound signal including noise that comes from the suppression direction is suppressed. As a result, the first subtraction unit 114 outputs a target sound signal OUT ($t_i$) in which a target sound from the sound reception direction is emphasized.

The gain $g(t_i)$ determines a subtraction amount of the sound signal in2($t_{i-1}$) to be subtracted from the sound signal in1($t_i$) by the first subtraction unit 114. In other words, the gain $g(t_i)$ determines a suppression amount of noise in the sound signal in1($t_i$) that includes the target sound. Moreover, a suppression amount of noise is determined by a state of noise because the gain $g(t_i)$ is determined by a state of noise as described above.

As described above, noise is suppressed when needed according to a state of noise or suppression processing is alleviated or stopped when the necessity to suppress noise is small. Accordingly, distortion of a target sound from a target sound source SS is suppressed while suppressing noise.

The microphone array device 100 may erroneously recognize that a target sound source SS in the sound reception range is present in the suppression direction. The erroneous recognition may be caused due to fluctuation of an incoming direction of the sound due to a movement of, for example, a speaker who is a target sound source SS, reflection from a wall, and surrounding environment such as an air flow. Even in the above case, distortion of the target sound may be suppressed when a degree of noise suppression is small because noise is suppressed according to the state of noise.

Identifying a direction of a sound source of noise with high steadiness by a microphone array is generally difficult. For example, noise with high steadiness generally comes from various directions and the noise level change is small. Thus, identifying the sound source direction is difficult. Therefore, the microphone array device 100 according to the embodiment reduces the suppression amount of the noise. In other words, the microphone array device 100 controls so as to suppress distortion of a target sound from the target sound source SS rather than to suppress noise when steadiness of noise is high. Meanwhile, identifying a sound source direction of noise with low steadiness is generally easy. Accordingly, the microphone array device suppresses the identified noise for the target sound.

(3) Processing Flow

Figure 5:
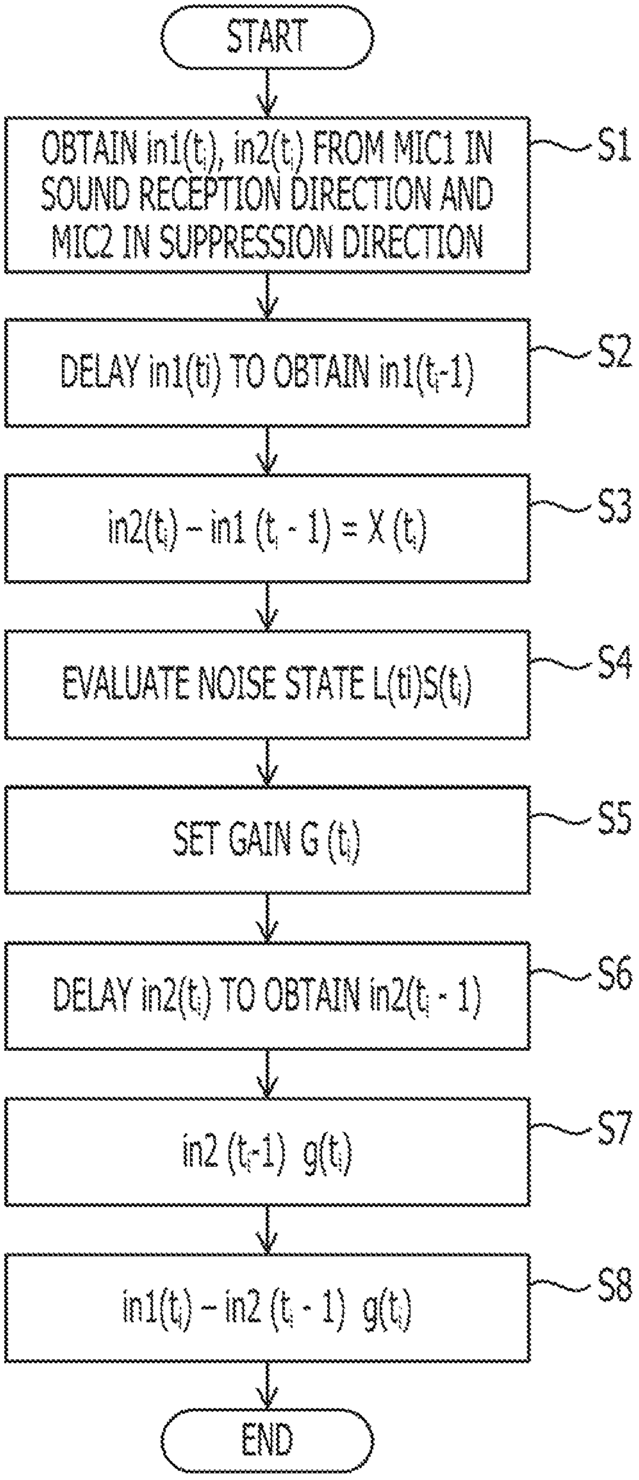
FIG. 5 is a flow chart illustrating noise suppression processing executed by the microphone array device according to the embodiment.

Hereinafter, processing according to the embodiment will be described by referring to FIG. 5. FIG. 5 is one example of a flow chart illustrating noise suppression processing executed by the microphone array device according to the embodiment.

Operation S1:

The first sound reception unit 111 obtains a sound signal in1($t_i$) that includes a target sound from the sound reception direction. The second sound reception unit 112 obtains a sound signal in2($t_i$) that includes noise from the suppression direction.

Operation S2:

The second delay unit 115 receives the sound signal in1($t_i$) that includes the target sound from the first sound reception unit 111 and generates a sound signal in1 ($t_{i-1}$) that is obtained by delaying the sound signal in1($t_i$) for a certain period Ta.

Operation S3:

The second subtraction unit 116 subtracts the sound signal in1($t_i$−1) from the sound signal in2($t_i$) and calculates a noise signal N($t_i$).

Operation S4:

The noise state evaluation unit 117 evaluates a state of noise based on a noise signal N($t_i$) that is an output from the second subtraction unit 116. The state of noise includes, for example, a noise level ($t_i$) and a noise level change S($t_i$).

Operation S5:

The subtraction adjustment unit 118 sets a gain g($t_i$) for adjusting a suppression amount of noise on a time axis according to a state of noise.

Operation S6:

The first delay unit 113 receives a sound signal in2($t_i$) that includes noise from the second sound reception unit 112 and generates a sound signal in2($t_{i-1}$) that is obtained by delaying the sound signal in2($t_i$) for a certain period Ta.

Operation S7:

The subtraction adjustment unit 118 multiplies the sound signal in2($t_{i-1}$) by the gain g(ti) and outputs the multiplication result to the first subtraction unit 114.

Operation S8:

The first subtraction unit 114 receives the sound signal in1($t_i$) that includes the target sound from the first sound reception unit 111 and subtracts the multiplication result from the sound signal in1($t_i$).

Second Embodiment

A microphone array device 200 according to a second embodiment obtains a state of noise by processing sound signals obtained by two microphones on a frequency axis and suppresses the noise by synchronous subtraction processing based on the state of noise. The hardware configuration of the microphone array device 200 according to the second embodiment is substantially the same as that of the first embodiment. Moreover, the same reference numerals are assigned to components that are the same as the first embodiment.

(1) Functional Configuration

Figure 6:
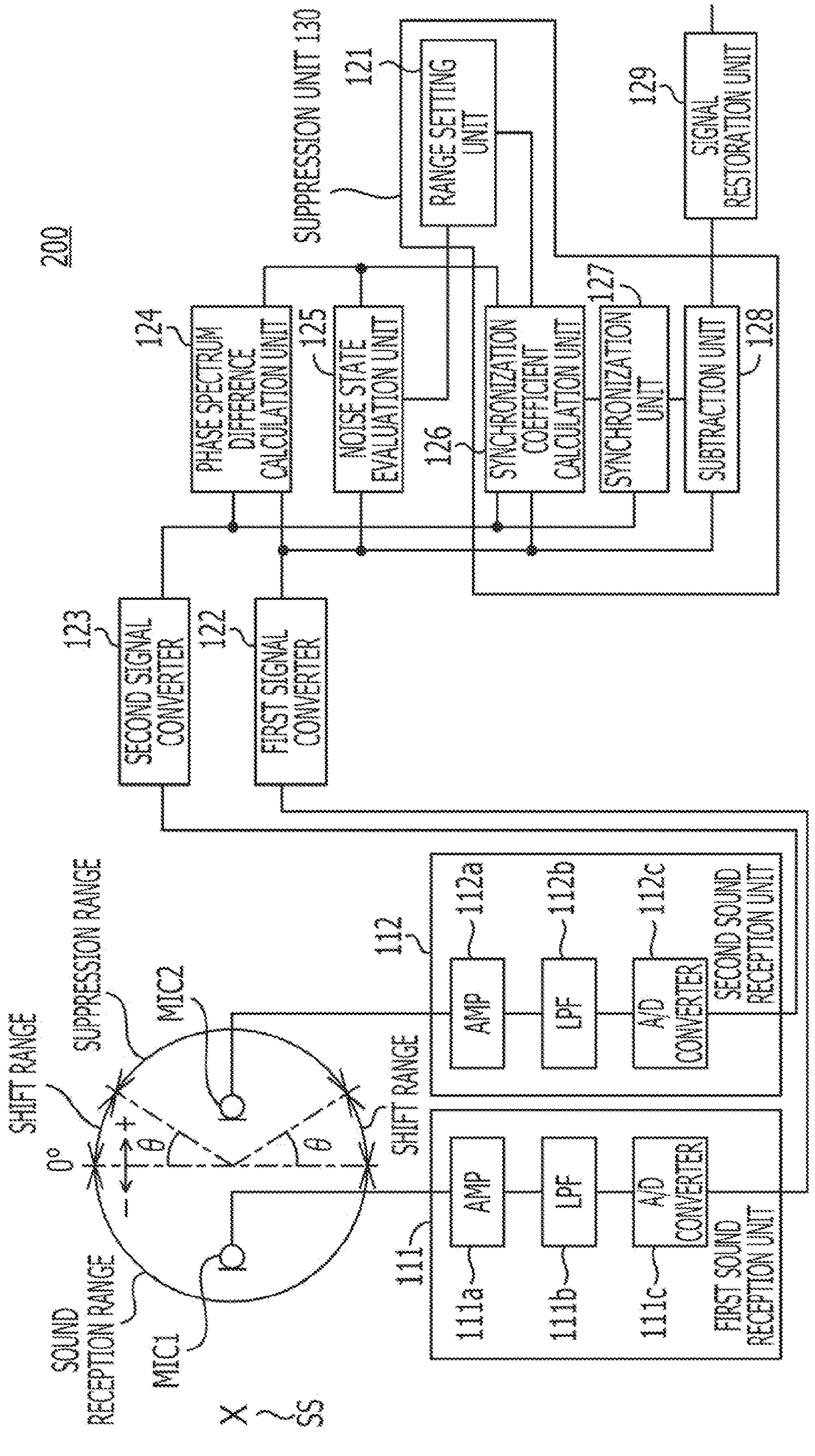
FIG. 6 is a block diagram illustrating a functional configuration of the microphone array device according to a second embodiment.

FIG. 6 is one example of a block diagram illustrating a functional configuration of the microphone array device according to the second embodiment. FIG. 6 illustrates a microphone MIC1 and a microphone MIC2 in a microphone array 104 of the microphone array device 200. Here, the microphone MIC1 and the microphone MIC2 are non-directional microphones.

In FIG. 6, a target sound source SS is present at the left side of the microphone MIC1 while a sound reception direction from where a target sound comes is set at the left side of the microphone MIC1. Moreover, a suppression direction is set at the right side of the microphone MIC2. For example, the suppression direction is 180 degrees opposite to the sound reception direction. A certain angle range that includes the target sound source SS is set as a sound reception range. A certain angle range that includes a suppression direction is set as a suppression range. A range between the sound reception range and the suppression range is set as a shift range. The shift range facilitates a gradual shift between the suppression range and the sound reception range and a gradual change in a degree of suppressing noise from the suppression range to the sound reception range.

In FIG. 6, the initial settings are as follows: the sound reception range is an angle range of 0 degree to $-\pi$, the shift range is an angle range of 0 degree to $\theta$ degree and $(\pi-\theta)$ degree to $\pi$, and the suppression range is $\theta$ degree to $(\pi-\theta)$ degree.

A microphone distance d between the microphone MIC1 and the microphone MIC2 is set substantially the same as that of the first embodiment.

Processing by functional units of the microphone array device 200 is executed in collaboration with the CPU 101, the ROM 102, the RAM 103, and the microphone array 104.

The microphone array device 200 includes a first sound reception unit 111, a second sound reception unit 112, a range setting unit 121, a first signal converter 122, a second signal converter 123, a phase spectrum difference calculation unit 124, a noise state evaluation unit 125, a synchronization coefficient calculation unit 126, a synchronization unit 127, a subtraction unit 128, and a signal restoration unit 129. According to the embodiment, a suppression unit 130 includes the range setting unit 121, the synchronization coefficient calculation unit 126, the synchronization unit 127, and the subtraction unit 128. Hereinafter, each of the functional units will be described.

(1-1) Range Setting Unit

The range setting unit 121 makes initial settings of a sound reception range, a shift range, and a suppression range for each microphone, for example, based on a user input. The microphone array device 200 accepts a user input through a user input acceptance unit (not illustrated) and the user input acceptance unit outputs the accepted user input to the range setting unit 121.

The range setting unit 121 may make initial settings of a sound reception range, a shift range, and a suppression range for each microphone based on initial values stored in the ROM102.

Moreover, the range setting unit 121 receives state of noise from the noise state evaluation unit 125 that include a noise level L(f), a noise level change S(f) and a combined value LS(f). The range setting unit 121 controls the sound reception range, the shift range, and the suppression range based on the state of the noise. Controlling the ranges will be described in a paragraph of the noise state evaluation unit 125.

(1-2) The First Sound Reception Unit and the Second Sound Reception Unit

The first sound reception unit 111 and the second sound reception unit 112 are substantially the same as those of the first embodiment. The first sound reception unit 111 samples a sound signal from the microphone MIC1 at a certain sampling frequency fs. The first sound reception unit 111 outputs a sound signal in1($t_i$) as a digital signal on a time axis. The second sound reception unit 112 samples a sound signal from the microphone MIC2 at a certain sampling frequency fs. The second sound reception unit 112 outputs a sound signal in2($t_i$) as a digital signal on a time axis.

(1-3) First Signal Converter and Second Signal Converter

The first signal converter 122 frequency-converts the sound signal in1($t_i$) on the time axis and generates a complex spectrum IN1($f$). The f here indicates a frequency. For example, a fast Fourier transform (FFT), a discrete cosine transform (DCT), and a wavelet transform may be used for the frequency conversion. A plurality of band pass filtering techniques such as subband decomposition may be used as well. Here, the first signal converter 122 uses the FFT and multiplies the sound signal in1($t_i$) by a window function while overlapping each signal interval. The first signal converter 122 applies an FFT to the multiplication result and generates a complex spectrum IN1($f$) on a frequency axis.

Likewise, the second signal converter 123 frequency-converts the sound signal in2($t_i$) on the time axis and generates a complex spectrum IN2($f$) on the frequency axis.

The complex spectrum IN1($f$) and the complex spectrum IN2($f$) are represented by the following expressions (8) and (9).

$$IN1(f)=W_1(f)\exp(j(2\pi f t_i+\phi 1(f))) \quad (8)$$

$$IN2(f)=W_2(f)\exp(j(2\pi f t_i+\phi 2(f))) \quad (9)$$

The f represents a frequency, $W_1$ and $W_2$ represent amplitudes, j represents a unit imaginary number, $\phi$1($f$) and $\phi$2($f$) represent phase delays that are functions of a frequency f. The $t_i$ represents time when a sound signal is fed to the microphone. The subscript $_i$ of t is a sampling number of each sound signal when the sound is taken in at sampling frequency fs. The subscript $_i$ is an integer of one or more.

The overlap window functions include hamming window function, Hanning window function, Blackman window function, 3 sigma Gaussian window function, and triangular window function.

(1-4) Phase Spectrum Difference Calculation Unit

The phase spectrum difference calculation unit 124 receives the complex spectrum IN1($f$) and the complex spectrum IN2($f$) from the first signal converter 122 and the second signal converter 123 respectively. The phase spectrum difference calculation unit 124 calculates a phase spectrum difference DIFF(f) for each frequency based on the complex spectrum IN1($f$) and the complex spectrum IN2($f$). The phase spectrum difference DIFF(f) represents a sound source direction for each frequency f between the microphone MIC1 and the microphone MIC 2 which are spaced apart by the distance d.

The phase spectrum difference DIFF(f) is represented by the following expression (10).

$$\begin{aligned} DIFF(f) &= \tan^{-1}(IN2(f)/IN1(f)) \\ &= \tan^{-1}((W_2(f)/W_1(f))\exp(j(\varphi 2(f)-\varphi 1(f)))) \end{aligned} \quad (10)$$

Figure 7:
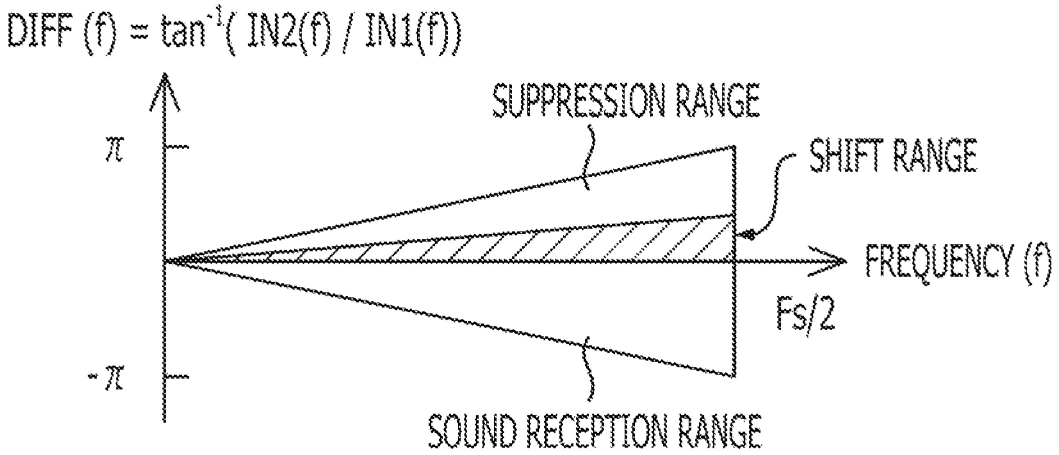
FIG. 7 illustrates a relationship between each frequency and a phase spectrum difference DIFF(f) ($-\pi \le DIFF(f) \le \pi$) of microphones MIC1 and the MIC2 arranged as illustrated in FIG. 6.

FIG. 7 illustrates a relationship between each frequency and phase spectrum difference DIFF(f) ($-\pi \leq DIFF(f) \leq \pi$) when each of the ranges is set as FIG. 6. In FIG. 7, a lower side of the horizontal axis is a sound reception range, an upper side of the horizontal axis is a shift range and a suppression range. The shaded area indicates the shift range.

The phase spectrum difference calculation unit 124 identifies a range where a sound source of an incoming sound is included based on the relationship in FIG. 7 and the phase spectrum difference DIFF(f). For example, when a phase spectrum difference DIFF(f) at a certain frequency f is in the suppression range in FIG. 7, the phase spectrum difference calculation unit 124 determines that a sound source of the incoming sound is in the suppression range. Moreover, when a phase spectrum difference DIFF(f) at a certain frequency f is in the shift range in FIG. 7, the phase spectrum difference calculation unit 124 determines that a sound source of the incoming sound is in the shift range.

The phase spectrum difference DIFF(f) is included in one of the sound reception range, the shift range, and the sound reception range because the microphone distance d is set by the expression (1) according to the first embodiment.

As described above, processing a sound signal for each certain frequency on the frequency axis allows a phase spectrum difference between each of the microphones to be detected more accurately than processing a sound signal on the time axis. For example, a target sound from a target sound source SS and noise generated at various frequencies by other plurality of sound sources coexist in a sound signal from the microphone MIC1 and a sound signal from the microphone MIC2. Hence, a sound source direction and a state of noise for each sound may be detected with higher accuracy by detecting a phase spectrum difference for each frequency.

(1-5) Noise State Evaluation Unit

The noise state evaluation unit 125 receives a range of a sound source of an incoming sound that is determined by the phase spectrum difference DIFF from the phase spectrum difference calculation unit 124. The noise state evaluation unit 125 evaluates a state of noise. The noise state evaluation unit 125 assumes an incoming sound is noise when the phase spectrum difference DIFF (f) is included in the suppression range in FIG. 7, in other words, the sound source of the incoming sound is included in the suppression range at a frequency f. As described above, the noise state evaluation unit 125 evaluates a state of noise when a sound source direction is included in the suppression range. In other words, the noise state evaluation unit 125 does not use a target sound the target sound source of which is in the sound reception range for evaluating a state of noise. The noise state evaluation unit 125 may evaluate a state of noise accurately based mostly on the noise itself.

The state of the noise includes, for example, a noise level and a noise level change, and examples of calculating the noise level and the noise level change will be described below.

(a) Calculating a state of noise (a1) Calculating a Noise Level L(f)

A method to calculate a noise level L(f) is described.

The noise state evaluation unit 125 calculates an average value of $|IN1(f)|$ based on the following expression (11) when a sound source of an incoming sound is included in the suppression range.

$$\text{average value of } |IN1(f)| = \beta\times(\text{average value of an analysis frame preceding } |IN1(f)|) + (1-\beta)\times|IN1(f)| \quad (11)$$

Here, the β represents a time constant to obtain an average value of |IN1(*f*)| and indicates an addition ratio or a combination ratio of the preceding analysis frame. The preceding analysis frame, here is a shift of an analysis window in the FFT, in other words, time which goes back for an amount of an overlap. The β is larger than 0 and less than 1.0.

Calculating an average of |IN1(*f*)| is substantially the same as applying a smoothing filter to |IN1(*f*)|, and in this case, the β is a time constant of the smoothing filter.

The noise state evaluation unit 125 calculates a relative level value (f) for a full scale of a noise level represented by an average value of |IN1(*f*)|. The |IN1(*f*)| that is a digital signal is represented by a bit. The full scale here is a ratio, represented by a decibel, of a substantially maximum value and a substantially minimum value for the level of the |IN1(*f*)| that is represented by a bit. For example, when the |IN1(*f*)| is represented by 16 bits, the ratio of the substantially maximum value and the substantially minimum value of the level of the |IN1(*f*)| is about 98 decibel. Accordingly, in this case, the full scale may be set to be 98 decibel. Note that a value of the full scale is changed according to the number of bits that represents the |IN1(*f*)|. Hereinafter, the |IN1(*f*)| is represented in 16 bits.

The relative level value (f) of the average value of |IN1(*f*)| is represented by the following expression (12).

$$\begin{aligned}\text{relative level value }(f) &= 10\log_{10}(\text{average value of } |IN1(f)|)^2 \quad (12)\\ &= 20\log_{10}(\text{average value of } |IN1(f)|)\end{aligned}$$

Moreover, the noise state evaluation unit 125 calculates a noise level L(f) based on a relationship between the noise level L(f) and the relative level value (f) that is set.

Figure 8:
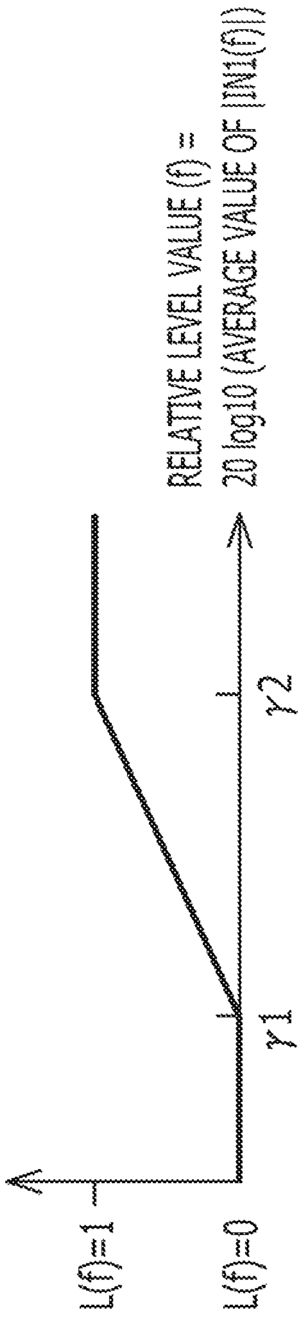
FIG. 8 illustrates a relationship between a noise level L(f) and a relative level value (f)

FIG. 8 illustrates a relationship between a noise level L(f) and a relative level value (f). The noise state evaluation unit 125 refers to the relationship in FIG. 8 and obtains a noise level corresponding to the relative level value (f) as described below. Note that the noise level L(f) is defined in a range of 0≤noise level L(f)≤1.0, and the level becomes higher as noise level L(f) is closer to 1.0, and the level is lower as noise level L(f) is closer to 0.

For example, when the relative level value (f) is larger than Y2 (relative level value (f)>Y2), in other words, the noise level is high, the noise state evaluation unit 125 calculates the noise level L(f) as 1.0. Moreover, when the relative level value (f) is smaller than Y1 (relative level value (f)<Y1), in other words, the noise level is low, the noise state evaluation unit 125 calculates the noise level L(f) as 0. For example, then is 58 db and the Y2 is 68 db, and the values may be obtained through an experiment.

When the relative level value (f) is Y1 or more and Y2 or less (Y1≤relative level value (f)≤Y2), for example, the noise level is calculated by a simple weighted average represented by the following expression (13). The simple weighted average is just one example, and an arithmetic average, a quadratic weighted average, and a cubic weighted average may be used as well.

$$\text{noise level } L(f) = (\text{relative level value }(f) - Y1)/(Y2 - Y1) \quad (13)$$

(a2) Calculating a Noise Level Change S(f)

A method to calculate a noise level change S(f) is described.

The noise state evaluation unit 125 calculates an average value of |IN1(*f*)| based on the above expression (11) when a sound source of an incoming sound is included in the suppression range.

The noise state evaluation unit 125 calculates a Rate(f) that is a ratio of |IN1(*f*)| to an average value of |IN1(*f*)| by the expression (14) below.

$$\text{Rate}(f) = |IN1(f)|/\text{average value of } |IN1(f)| \quad (14)$$

Figure 9:
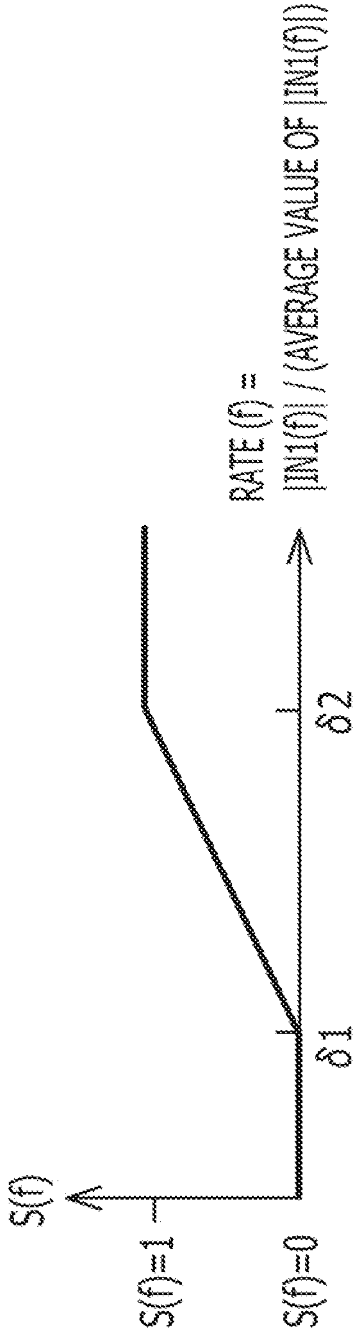
FIG. 9 illustrates a relationship between a noise level change S(f) and a Rate(f)

Moreover, the noise state evaluation unit 125 calculates the noise level change S(f) based on a relationship between the noise level change S(f) and the Rate(f) that is set. FIG. 9 illustrates a relationship between the noise level change S(f) and the rate (f). Note that the noise level change S(f) is defined in a range of 0≤noise level change S(f)≤1.0. It is assumed that the noise level change is larger as the noise level change is closer to 1.0, and the steadiness is low. The noise state evaluation unit 125 refers to the relationship illustrated in FIG. 9 and obtains a noise level change S(f) corresponding to the Rate(f).

For example, when the Rate(f) is larger than δ2 (Rate(f)>δ2), the noise state evaluation unit 125 calculates the noise level change S(f) as 1.0. When the Rate(f) is smaller than δ1 (Rate(f)<δ1), the noise state evaluation unit 125 calculates the noise level change S(f) as 0. For example, the δ1 is 0.7, and δ2 is 1.4, and the values may be obtained by an experiment.

The noise level change S(f) is calculated, for example, by a simple weighted average represented in the expression (15) below when the Rate(f) is δ1 or more, and δ2 or less (δ1≤Rate(f)≤δ2). The simple weighted average is just one example, and an arithmetic average, a quadratic weighted average, and a cubic weighted average may be used as well.

(a3) Calculating a Combined Value LS(f)

The noise state evaluation unit 125 calculates a combined value LS(f) as a function in which both the noise level L(f) and the noise level change S(f) are variables. The combined value LS(f), may be calculated by a simple weighted average of the noise level L(f) and the noise level change S(f) using the expression (16) below.

$$\text{Combined value } LS(f) = \tau\times L(f) + (1-\tau)\times S(f) \quad (16)$$

The τ here determines a ratio that the noise level L(f) and the noise level change S(f) to the combined value LS(f), and may be obtained by an experiment. Moreover, the τ is defined in a range of 0≤τ≤1.0.

The combined value LS(f) is defined in a range of 0≤combined value LS(f)≤1.0. The combined value LS(f) approaches 1.0 as the noise level change S(f) is greater. Conversely, the combined value LS(f) approaches 0 as the noise level L(f) and the noise level change S(f) are smaller.

The noise state evaluation unit 125 increases τ when a state that noise level L(f)<noise level change S(f) continues for a certain period. Accordingly, the noise state evaluation unit 125 reduces an impact of the noise level change S(f) on the combined value LS(f) under a state of noise level L(f)<noise level change S(f). Conversely, the noise state evaluation unit 125 decreases τ when a state that noise level L(f)>noise level change S(f) continues for a certain period. Accordingly, the noise state evaluation unit 125 reduces an impact of the noise level L(f) on the combined value LS(f) under a state that noise level L(f)>noise level change S(f). Through the above described processing, the combined value LS(f) may become a function in which both the noise level L(f) and the noise level change S(f) are appropriately taken account of.

(b) Controlling Ranges Based on a State of Noise by a Range Setting Unit

A method to control the sound reception range, the shift range, and the suppression range based on a state of noise will be described.

The range setting unit 121 receives a state of noise that includes the noise level L(f) and the noise level change S(f). The range setting unit 121 controls the sound reception range, the shift range, and the suppression range based on the state of noise. In other words, the range setting unit 121 controls directivity of the microphone array that includes the microphone MIC1 and the microphone MIC2. FIGS. 10 to 13 illustrate an example of a method to control the sound reception range, the shift range, and the suppression range. FIG. 11 illustrates the range control in FIG. 10 by a relationship between each frequency and a phase spectrum difference DIFF(f) ($-\pi \le$DIFF(f)$\le \pi$). FIG. 13 illustrates the range control in FIG. 12 by a relationship between each frequency and a phase spectrum difference DIFF(f) ($-\pi \le$DIFF(f)$\le \pi$).

Figure 10:
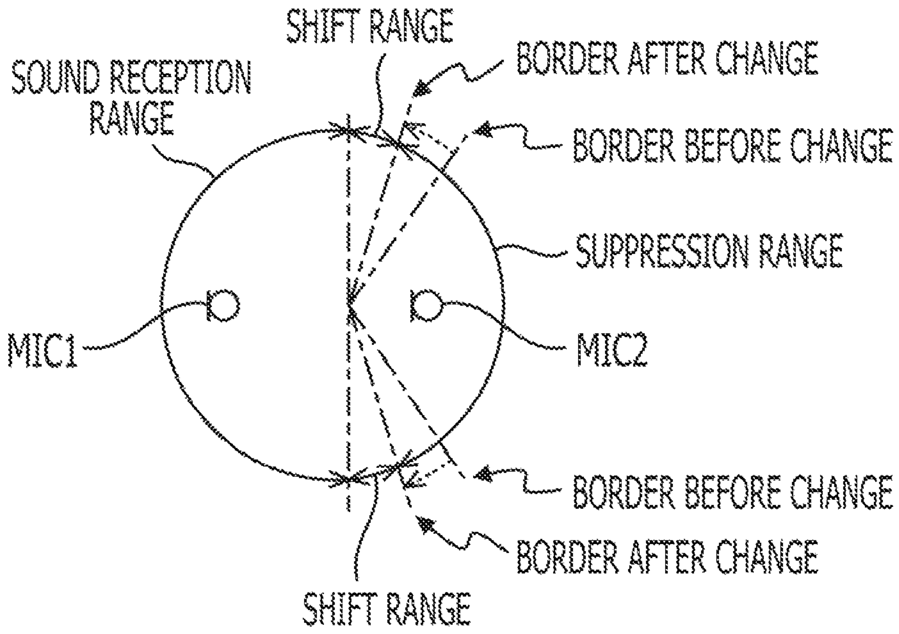
FIG. 10 illustrates an example of a method to control a sound reception range, a shift range, and a suppression range.
Figure 11:
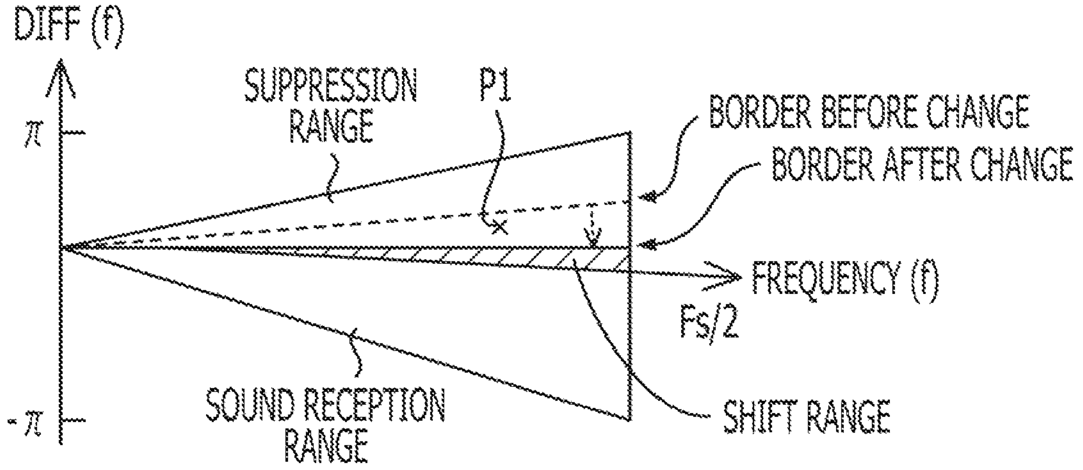
FIG. 11 illustrates an example of a method to control a sound reception range, a shift range, and a suppression range.

FIG. 10 is described. The range setting unit 121 expands the suppression range by narrowing the shift range if the noise level L(f) is high. For example, when the noise level L(f)=1.0, the range setting unit 121 expands the suppression range by narrowing the shift range. In FIG. 10, a border between the shift range and the suppression range shifts to the sound reception side after the change. The range setting unit 121 may control directivity of the microphone array so as to efficiently suppress noise the sound source of which is the suppression range by expanding the suppression range. The target sound from the target sound source SS may be efficiently collected while suppressing the noise because the suppression range and the shift range are adjusted without changing the reception range. Note that the reception range may be narrowed.

The range setting unit 121 controls each range in the same manner as FIG. 10 when the noise level change S(f) is large and the steadiness is low, and for example, the noise level change S(f) is 1.0. Moreover, the range setting unit 121 controls each range in the same manner as FIG. 10, for example, when the combined value LS(f)=1.0.

In FIG. 11, control of each range in FIG. 10 is illustrated by a relationship between each frequency and a phase spectrum difference DIFF(f). In FIG. 11, a lower side of the horizontal axis is the sound reception range, an upper side of the horizontal axis is the shift range and the suppression range. The shaded area is the shift range. The point P1 indicates a position of a phase spectrum difference DIFF(f) at a certain frequency f. The point P1 is in the shift range before narrowing the shift range, and is in the suppression range after narrowing the shift range. Accordingly, an effect of suppressing noise that exhibits characteristics as the point P1 is increased more after changing the shift range than before the changing. Controlling the ranges by expanding the suppression range while narrowing the shift range achieves efficient noise suppression.

Figure 12:
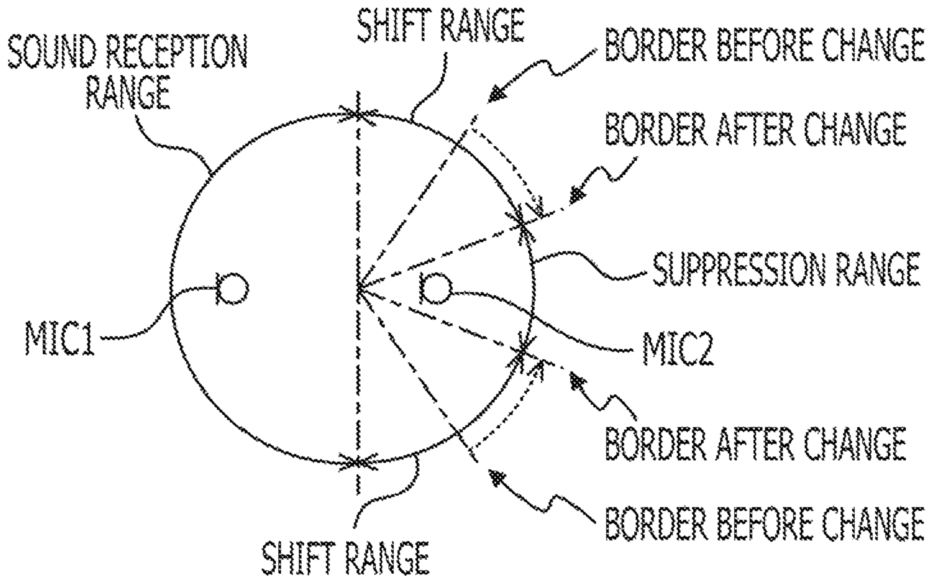
FIG. 12 illustrates an example of a method to control a sound reception range, a shift range, and a suppression range.
Figure 13:
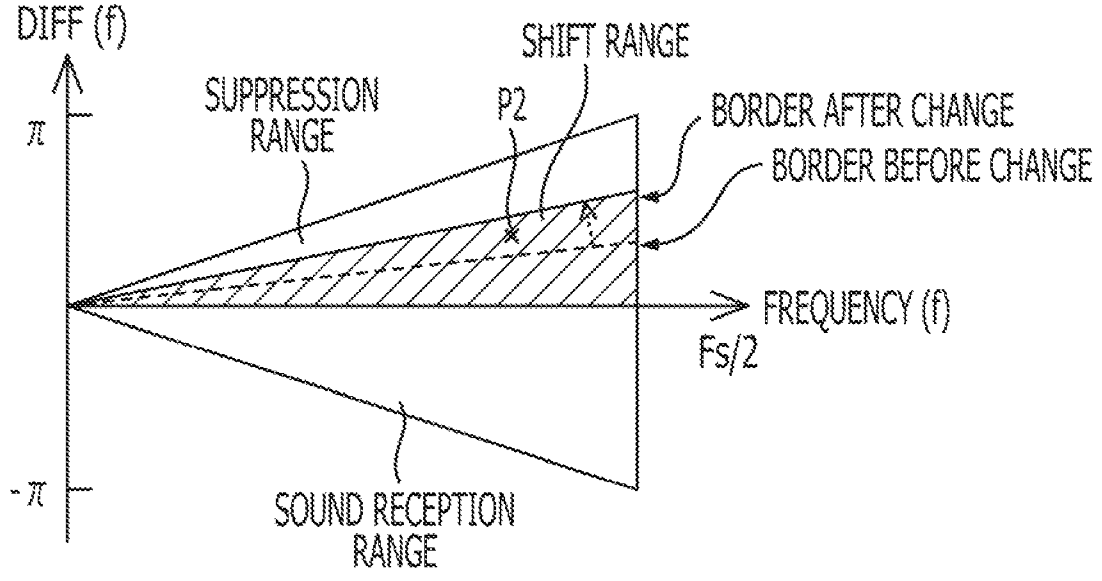
FIG. 13 illustrates an example of a method to control a sound reception range, a shift range, and a suppression range.

FIG. 12 is described. The range setting unit 121 narrows the suppression range by expanding the shift range when the noise level L(f) is low. For example, the range setting unit 121 expands the shift range when the noise level L(f)=0. In FIG. 12, a border between the shift range and the suppression range shifts to the suppression range side after the change. Narrowing the suppression range suppresses distortion of a target sound from the target sound source SS in the sound reception range. Moreover, the microphone array device may control directivity of the microphone array so that noise the sound source of which is in the suppression range may be suppressed as well. Expanding the shift range allows the microphone array device to shift gradually from the reception range to the suppression range and to reduce a degree of noise suppression.

The microphone array device 200 may erroneously recognize a target sound source SS that is actually in the sound reception range is present in a shift direction. The erroneous recognition may be caused due to fluctuation of an incoming direction of a sound due to a movement of, for example, a speaker who is a target sound source SS and surrounding environment. Even in the above case, controlling the ranges as illustrated in FIG. 12 allows to reduce a degree of noise suppression, and to suppress distortion of the target sound.

The range setting unit 121 controls each range in the same manner as in FIG. 12 when a noise level change S(f) is small and the steadiness is high, for example, the noise level change S(f)=0. Moreover, the range setting unit 121 controls each range in the same manner as in FIG. 12 when the combined value LS(f) is small, for example, the combined value LS(f)=0.

FIG. 13 illustrates the range control in FIG. 12 by a relationship of each frequency and a phase spectrum difference DIFF(f). The point P2 indicates a position of a phase spectrum difference DIFF(f) at a certain frequency f. The point P2 is in the suppression range before expanding the shift range, and is in the shift range after expanding the shift range. Accordingly, an effect of suppressing noise that exhibits characteristics as the point P2 is decreased more after changing the shift range than before the changing. Controlling the ranges by expanding the shift range while narrowing the suppression range allows to reduce an amount of suppressing noise and to suppress distortion of the target sound.

In the above description, the range setting unit 121 controls typically the shift range and the suppression range. However, the sound reception range may be controlled as well. For example, in FIGS. 10 and 11, when the noise level L(f) is high, the range setting unit 121 narrows the sound reception range to expand the suppression range, or narrows both the sound reception range and the shift range to expand the suppression range. In FIGS. 12 and 13, when the noise level L(f) is low, the range setting unit 121 expands the sound reception range to narrow the suppression range, or expands both the sound reception range and the shift range to narrow the suppression range.

(1-6) Synchronization Coefficient Calculation Unit

The synchronization coefficient calculation unit 126 receives information on the sound reception range, the shift range, and the suppression range that are set based on a state of noise from the range setting unit 121. The synchronization coefficient calculation unit 126 receives a phase spectrum difference DIFF(f) from the phase spectrum difference calculation unit 124. The synchronization coefficient calculation unit 126 calculates synchronization coefficients as will be described in (a1) to (a3) below based on the sound reception range, the shift range, and the suppression range that are set based on a state of noise and the phase spectrum difference DIFF(f).

(a) Synchronization Coefficient C(f)

(a1) when the Phase Spectrum Difference DIFF(f) is in the Suppression Range

The synchronization coefficient calculation unit 126 calculates a synchronization coefficient C(f) when the phase spectrum difference DIFF(f) is in the suppression range.

The synchronization coefficient calculation unit 126 makes the following estimation on noise obtained by the microphone MIC1. A sound obtained by the microphone MIC1 for a specific frequency f includes noise from the suppression range. The synchronization coefficient calculation unit 126 estimates that the noise obtained by the microphone MIC1 is substantially the same noise included in a sound obtained by the microphone MIC2 and the noise reaches the microphone MIC1 after delaying for a phase spectrum difference DIFF(f).

$$\text{synchronization coefficient } \alpha\times C(f)'+(1-\alpha)\times(\text{IN1}(f)/\text{IN2}(f)) \quad (17)$$

Here, the C(f)' is a synchronization coefficient before an update. The synchronization coefficient C(f) may be updated, for example, for each analysis frame. The α represents an addition ratio or a combination ratio of a phase delay amount of a preceding analysis frame for synchronization. The α is larger than 0 and less than 1.0.

(a2) When a Phase Spectrum Difference DIFF(f) is in the Sound Reception Range

The synchronization coefficient calculation unit 126 calculates a synchronization coefficient C(f) based on the following expressions (18) or (19) when the phase spectrum difference DIFF(f) is in the sound reception range.

$$\text{synchronization coefficient } C(f)=\exp(-2\pi f/fs) \quad (18)$$

$$\text{synchronization coefficient } C(f)=0 \quad (19)$$

(a3) When a Phase Spectrum Difference DIFF(f) is in the Shift Range

The synchronization coefficient calculation unit 126 applies, for example, a weighted average to a calculated result of the synchronization coefficient C(f) based on the above-described (a1) and (a2). Accordingly, the synchronization coefficient calculation unit 126 calculates a synchronization coefficient C(f).

An example of calculating a synchronization coefficient C(f) will be described by referring to FIGS. 11 and 13 again. In FIG. 11, the point P1 is in the shift range before narrowing the shift range. However, the point P1 is in the suppression range after narrowing the shift range. Thus, the synchronization coefficient calculation unit 126 calculates a synchronization coefficient C(f) based on a weighted average of the above described (a3). Meanwhile, the synchronization coefficient calculation unit 126 calculates a synchronization coefficient C(f) based on the expression (17) at the suppression range after changing the range.

In FIG. 13, the point P2 is in the suppression range before expanding the shift range. However, the point P2 is in the shift range after expanding the shift range. Thus, the synchronization coefficient calculation unit 126 calculates a synchronization coefficient C(f) based on the above described expression (17) at the suppression range before changing the range. Meanwhile, the synchronization coefficient calculation unit 126 calculates a synchronization coefficient C(f) based on the above described weighted average of (a3) after changing the range.

Synchronization Coefficient Cg(f) that is Dependent of the Gain g(f)

The synchronization coefficient calculation unit 126 may calculate the synchronization coefficient Cg(f) that is dependent of the gain g(f) by further multiplying the synchronization coefficient C(f) that is calculated based on the above (a1) to (a3) by a gain g(f).

$$\text{synchronization coefficient } Cg(f)=\text{gain } g(f)\times \text{synchronization coefficient } C(f) \quad (20)$$

Figure 14:
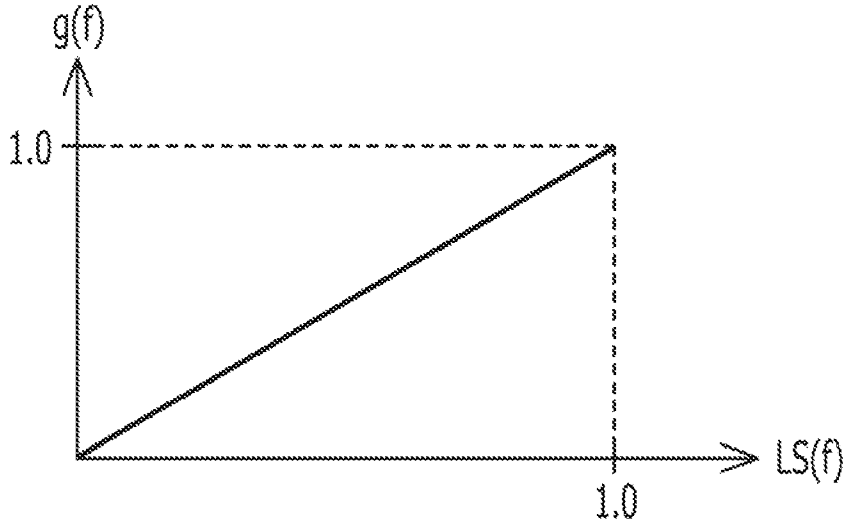
FIG. 14 illustrates one example of a relationship between a combined value LS(f) that indicates a state of noise and a gain g(f)

The gain g(f) is a value to adjust a suppression amount of noise on a frequency axis. The synchronization coefficient calculation unit 126 sets the gain g(f) according to a state of noise. FIG. 14 illustrates one example of a relationship between a combined value LS(f) that indicates a state of noise and a gain g(f). The synchronization coefficient calculation unit 126 sets a gain g(f) based on the combined value LS(f) calculated by the above-described expression (16) and FIG. 14. The gain g(f) is 0 or more and 1.0 or less. A subtraction unit 128, which will be described later, performs processing by using the synchronization coefficient Cg(f) that is dependent of the gain g(f), and thereby adjusts an amount to subtract a complex spectrum IN2(*f*) from a complex spectrum IN1(*f*). As a result, a suppression amount of noise included in a sound obtained by the microphone MIC 1 is adjusted.

Here, the gain g(f) is calculated based on the combined value LS(f). However, the gain g(f) may be calculated based on a noise level L(f) or a noise level change S(f).

(1-7) Synchronization Unit

The synchronization unit 127 receives the synchronization coefficient C(f) or the synchronization coefficient Cg(f) that is dependent of the gain g(f) from the synchronization coefficient calculation unit 126. The synchronization unit 127 performs synchronization by using the synchronization coefficient C(f) or the synchronization coefficient Cg(f) based on the state of noise. Alternatively, the synchronization unit 127 may perform synchronization based on an initial setting that specify which of the synchronization coefficients is used.

For example, when the synchronization coefficient Cg(f) is used, the synchronization unit 127 multiplies the complex spectrum IN2(*f*) by the synchronization coefficient Cg(f) as represented by the expression (21) below. Accordingly, a complex spectrum INs2(*f*) that is obtained by synchronizing the complex spectrum IN2(*f*) with the complex spectrum IN1(*f*) is calculated.

$$\text{IN}s2(f)=Cg(f)\times\text{IN2}(f) \quad (21)$$

Here, the Cg(f) is used as a synchronization coefficient; however the C(f) may be used instead.

(1-8) Subtraction Unit

As represented in the following expression (22), the complex spectrum INs2(*f*) that is synchronized is subtracted from the complex spectrum IN1(*f*) to obtain an output OUT(f).

$$\text{OUT}(f)=\text{IN1}(f)-\text{IN}s2(f) \quad (22)$$

(1-9) Signal Restoration Unit

The signal restoration unit 129 converts the output OUT(f) from the subtraction unit 128 into a signal on a time axis. Processing by the signal restoration unit 129 is inverse to conversions by the first signal converter 122 and the second signal converter 123. Here, the signal restoration unit 129 applies an inverse Fast Fourier Transform (IFFT) to the output OUT(f). Moreover, the signal restoration unit 129 performs an overlap add operation for the result of the IFFT to generate an output signal of the microphone MIC1 on a time axis.

(2) Processing Flow

Figure 15:
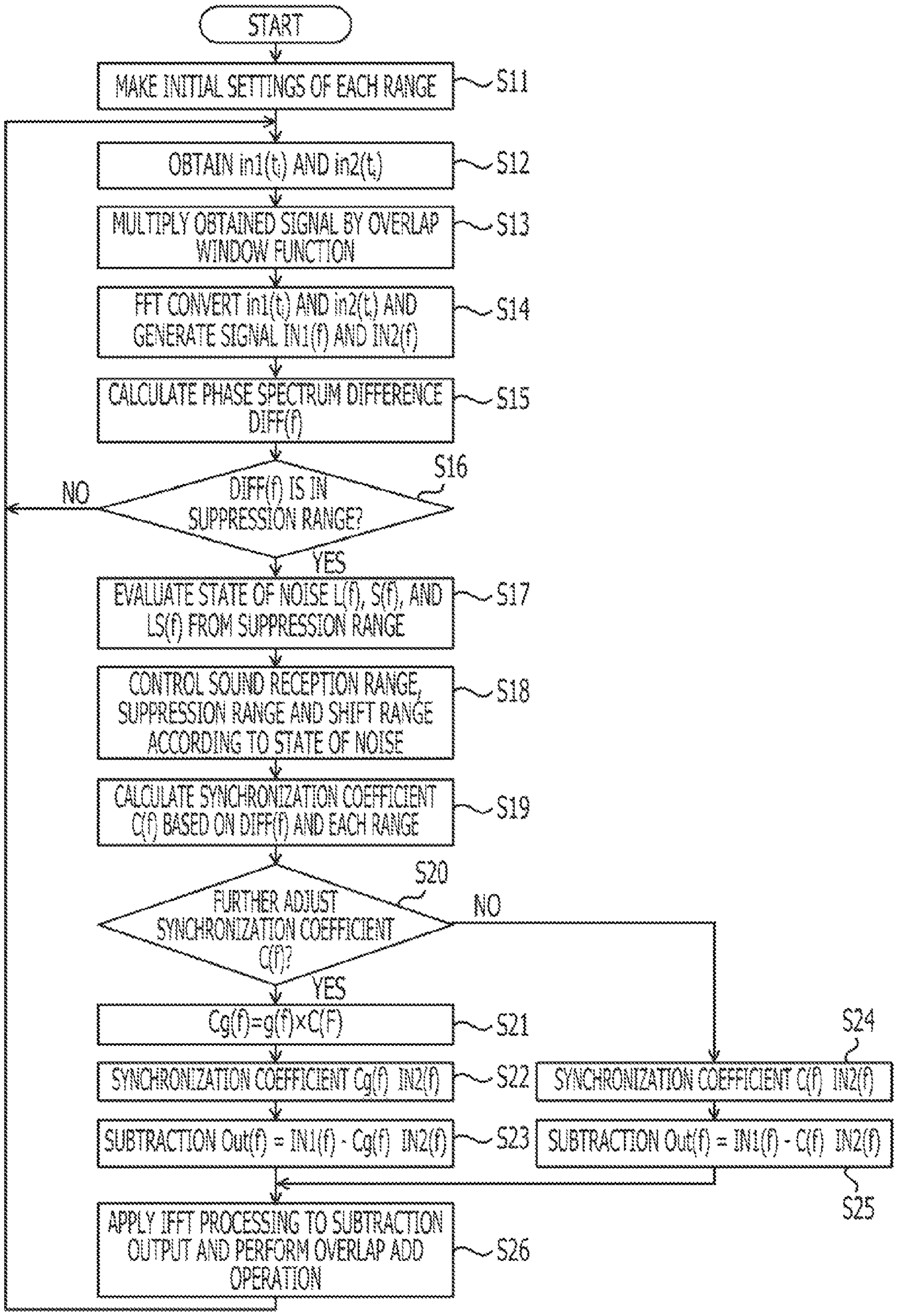
FIG. 15 is a flow chart illustrating noise suppression processing executed by the microphone array device according to the embodiment.

Hereinafter, processing according to the embodiment will be described by referring to FIG. 15. FIG. 15 is one example of a flow chart illustrating noise suppression processing executed by the microphone array device according to the embodiment.

Operation S11

The range setting unit 121 makes initial settings of a sound reception range, a shift range, and a suppression range for each microphone, for example, based on a user input.

Operation S12

The first sound reception unit 111 and the second sound reception unit 112 obtain a sound signal in1($t_i$) and a sound signal in2($t_i$) on a time axis.

Operation S13 and Operation S14

The first signal converter 122 multiplies each signal interval of the sound signal in1($t_i$) by an overlap window function (Operations S13) and generates a complex spectrum IN1($f$) on a frequency axis by further applying the FFT (Operation S14). Likewise, the second signal converter 123 frequency-converts the sound signal in2($t_i$) to generate a complex spectrum IN2($f$) on the frequency axis.

Operation S15:

The phase spectrum difference calculation unit 124 calculates a phase spectrum difference DIFF(f) between a complex spectrum IN1($f$) and a complex spectrum IN2($f$) for each frequency.

Operation S16:

The phase spectrum difference calculation unit 124 determines a range in which the phase spectrum difference DIFF(f) is included among the sound reception range, the shift range, and the suppression range. When the phase spectrum difference DIFF(f) is included in the suppression range, the process proceeds to Operation S17, otherwise, returns to Operation S12.

Operations S17:

The noise state evaluation unit 125 assumes an incoming sound as noise and evaluates the state of noise when the phase spectrum difference DIFF(f) is included in the suppression range, in other words, the sound source of the incoming sound is included in the suppression range. The state of noise includes, for example, a noise level L(f), a noise level change S(f), and a combined value LS(f) of the noise level L(f) and the noise level change S(f).

Operation S18:

The range setting unit 121 obtains the state of noise from the noise state evaluation unit 125 and controls directivity of the microphone array by controlling the sound reception range, the shift range, and the suppression range based on the state of noise.

Operation S19

The synchronization coefficient calculation unit 126 calculates the synchronization coefficient C(f) based on the sound reception range, the shift range, and the suppression range that are set based on the state of noise and the phase spectrum difference DIFF(f).

Operation S20

When the synchronization coefficient C(f) is further adjusted to calculate the synchronization coefficient Cg(f) that is dependent of the gain g(f), the process proceeds to Operation S21, otherwise, returns to Operation S24.

Operation S21:

The synchronization coefficient calculation unit 126 multiplies the synchronization coefficient C(f) by the gain g(f) to calculate the synchronization coefficient Cg(f) that is dependent of the gain g(f). The gain g(f) is a numerical value to adjust a suppression amount of noise on the frequency axis.

Operation S22:

The synchronization unit 127 multiplies the complex spectrum IN2($f$) by the synchronization coefficient Cg(f) to synchronize the complex spectrum IN2($f$) with the complex spectrum IN1 (1).

Operation S23:

The subtraction unit 128 subtracts the multiplication result of Operation S22 from the complex spectrum IN1($f$) to obtain an output OUT(f).

Operation S24:

The synchronization unit 127 multiplies the complex spectrum IN2($f$) by the complex spectrum C(f) to synchronize the complex spectrum IN2($f$) with the complex spectrum IN1 (1).

Operation S25:

The subtraction unit 128 subtracts the multiplication result of Operation S24 from the complex spectrum IN1($f$) to obtain an output OUT(f).

Operation S26:

The signal restoration unit 129 converts the output OUT(f) from the subtraction unit 128 to a signal on the time axis and further performs an overlap add operation and outputs an output signal in a time domain of the microphone MIC1. After completing the processing, the process returns to Operation S12 and the above described processing is repeated at an interval, for example, based on a certain sampling frequency.

The microphone array device 200 according to the embodiment controls the sound reception range, the shift range, and the suppression range according to a state of noise, and therefore may suppress noise according to the state of noise. For example, when a noise level L(f) is high, the microphone array device 200 may efficiently suppress noise the sound source of which is in the suppression range by narrowing the shift range to expand the suppression range.

The microphone array device 200 according to the embodiment may suppress noise the sound source of which is in the suppression range while suppressing distortion of a target sound from a target sound source SS as well by expanding the shift range to narrow the suppression range for example when the noise level L(f) is small. At this time, shifting from the sound reception range to the suppression range is gradual because the shift range is expanded. As a result, the microphone array device 200 according to the embodiment may gradually change a degree of noise suppression.

Even if a target sound source SS that is actually in the sound reception range is erroneously recognized present in the shift range, a degree of suppressing an incoming sound that comes to the microphone array device 200 from the shift range may be reduced depending on the state of noise. For example, as described above, when the shift range is expanded, the degree of suppressing the target sound that is erroneously recognized as noise is reduced, and distortion of the target sound from the target sound source SS may be suppressed.

As described above, noise is suppressed according to a state of noise, and therefore according to how much the noise needs to be suppressed. Hence, distortion of a target sound may be suppressed.

Third Embodiment

A microphone array device 300 according to a third embodiment obtains a state of noise by processing sound signals obtained by two microphones on a frequency axis. Moreover, the microphone array device 300 suppresses noise by adjusting a gain for adjusting a suppression amount of noise based on the state of noise.

The hardware configuration of the microphone array device 300 according to the third embodiment is substantially the same as that of the first embodiment. Moreover, the same reference numerals are assigned to components that are the same as the second embodiment.

(1) Functional Configuration

Figure 16:
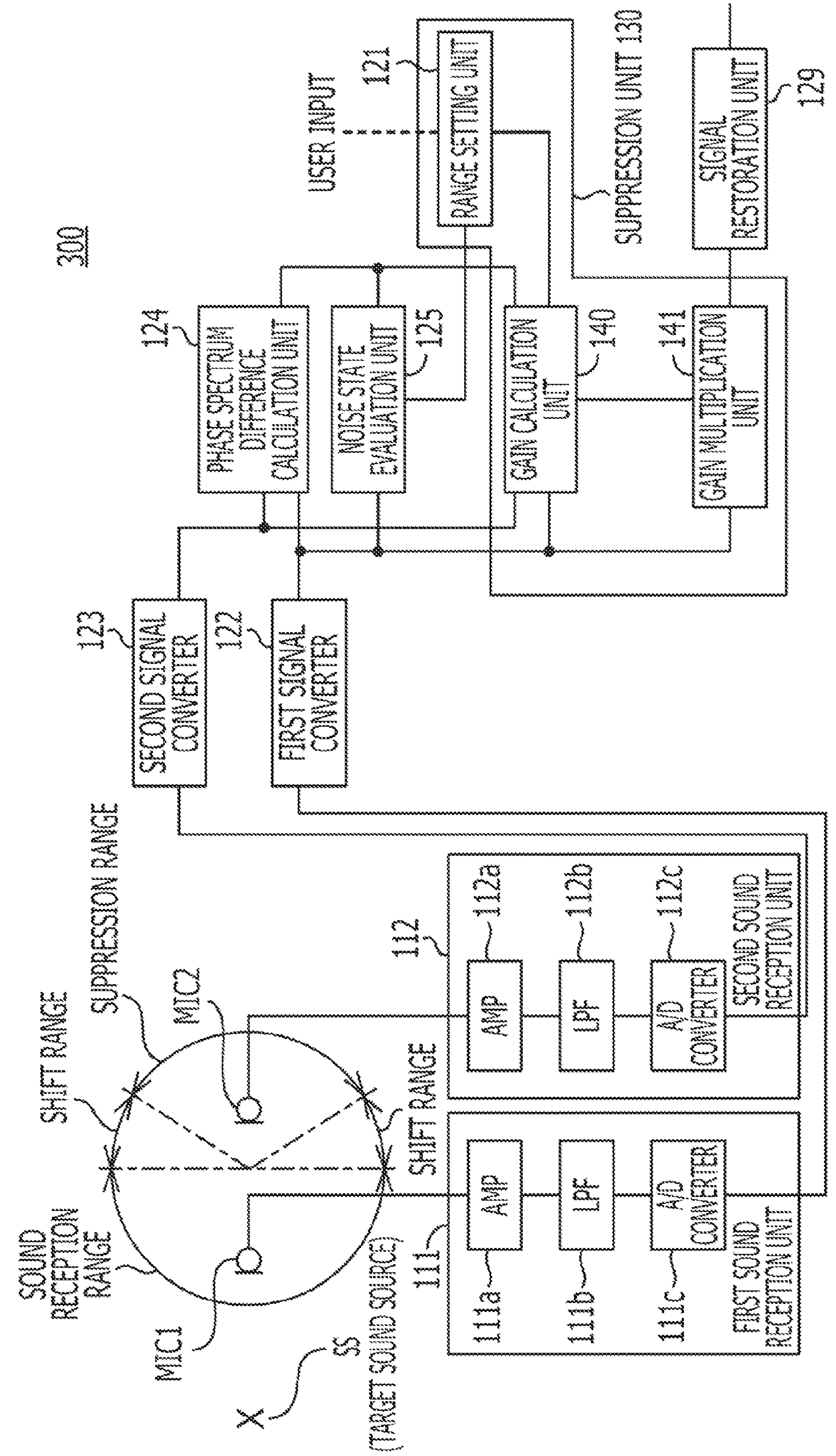
FIG. 16 is a block diagram illustrating a functional configuration of a microphone array device according to a third embodiment.

FIG. 16 is one example of a block diagram illustrating a functional configuration of the microphone array device according to the third embodiment. The microphone array device 300 according to the third embodiment includes, as in the microphone array device 200 according to the second embodiment, a first sound reception unit 111, a second sound reception unit 112, a range setting unit 121, a first signal converter 122, a second signal converter 123, a phase spectrum difference calculation unit 124, a noise state evaluation unit 125, and a signal restoration unit 129. Processing by the above-described functional units is substantially the same as that of the second embodiment.

Hereinafter, a gain calculation unit 140 and a gain multiplication unit 141 will be described. In the third embodiment, the suppression unit 130 includes the range setting unit 121 and the gain calculation unit 140.

(1-1) Gain Calculation Unit

The gain calculation unit 140 receives information on a sound reception range, a shift range, and a suppression range that are set based on a state of noise from the range setting unit 121. Moreover, the gain calculation unit 140 receives a phase spectrum difference DIFF(f) from the phase spectrum difference calculation unit 124. The gain calculation unit 140 calculates a gain G(f) for adjusting a suppression amount of noise on a frequency axis based on the sound reception range, the shift range, and the suppression range that are set based on a state of noise, and the phase spectrum difference DIFF(f). The gain g(f) is 0 or more and 1.0 or less.

For example, the gain calculation unit 140 sets a gain G(f) to 1.0 when the phase spectrum difference DIFF(f) is included in the sound reception range, and to 0 when the phase spectrum difference DIFF(f) is included in the suppression range. Moreover, the gain calculation unit 140 obtains a simple weighted average of the gain G(f) in the suppression range and the gain G(f) in the sound reception range according to a position of the phase spectrum difference DIFF(f) when the phase spectrum difference DIFF(f) is included in the shift range. The simple weighted average is just one example, and an arithmetic average, a quadratic weighted average, and a cubic weighted average may be used as well.

Adjusting the gain G(f) by the gain calculation unit 140 adjusts an amount to suppress a level of the complex spectrum IN1(*f*) by the gain multiplication unit 141. The microphone array device 300 adjusts an amount of suppressing noise included in a sound obtained by the microphone MIC1. Furthermore, the gain G(f) may be updated at each sampling of a sound signal.

Figures 17A, 17B, 17C:
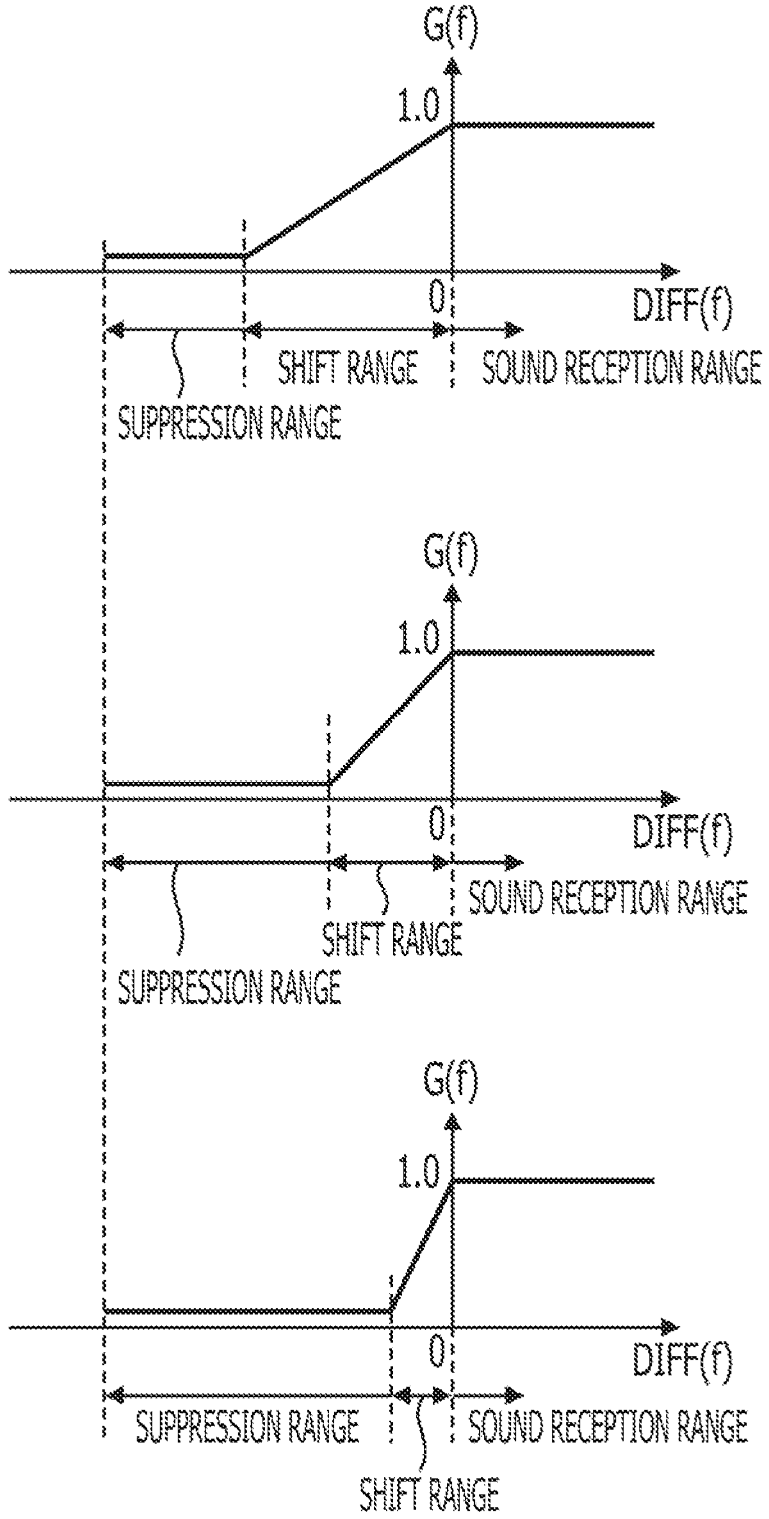
FIG. 17A illustrates a sound reception range, a shift range, and a suppression range that are changed from initial settings.
FIG. 17B illustrates a relationship between a gain G(f) and a phase spectrum difference DIFF(f) under a state that a sound reception range, a shift range, and a suppression range are in the initial settings.
FIG. 17C illustrates a sound reception range, a shift range, and a suppression range that are changed from the initial settings.

FIGS. 17A to 17C illustrate a relationship between the sound reception range, the shift range, and the suppression range, and the gain G(f).

FIG. 17B illustrates a relationship between a gain G(f) and a phase spectrum difference DIFF(f) under the initial settings of the sound reception range, the shift range, and the suppression range.

The range setting unit 121 sets each range, for example, as illustrated in FIG. 17A, when a noise level L(f) obtained from the noise state evaluation unit 125 is low, or a change in a noise level S(f) is small. Here, the range setting unit 121 narrows the suppression range by expanding the shift range more compared with that in FIG. 17B. The gain G(f) is gradually reduced from the sound reception range to the suppression range because the shift range is expanded. Therefore, a gradual shift from the sound reception range to the suppression range may be achieved, and the microphone array device 300 reduces a degree of suppressing noise. Accordingly, the microphone array device 300 may suppress distortion of the target sound even if a sound source of an incoming sound is shifted from the sound reception range to the shift range because the degree of suppression is small.

Meanwhile, the range setting unit 121 sets each range, for example, as illustrated in FIG. 17C when a noise level L(f) obtained from the noise state evaluation unit 125 is high, or a noise level change S(f) is large. Here, the range setting unit 121 expands the suppression range by narrowing the shift range more compared with that in FIG. 17B. The gain G(f) is sharply reduced from the sound reception range to the suppression range because the shift range is narrowed. Hence, the microphone array device 300 may efficiently suppress noise the sound source of which is in the suppression range.

(1-2) Gain Multiplication Unit

The gain multiplication unit 141 obtains a gain G(f) from the gain calculation unit 140. The gain multiplication unit 141 multiplies the complex spectrum IN1(*f*) by the gain G(f) to output an OUT(f) as represented by the following expression (23).

$$OUT(f)=IN1(f)\times G(f) \quad (23)$$

The OUT(f) is processed by the signal restoration unit 129 and is output as an output signal of the microphone MIC1 on a time axis.

Processing Flow

Figure 18:
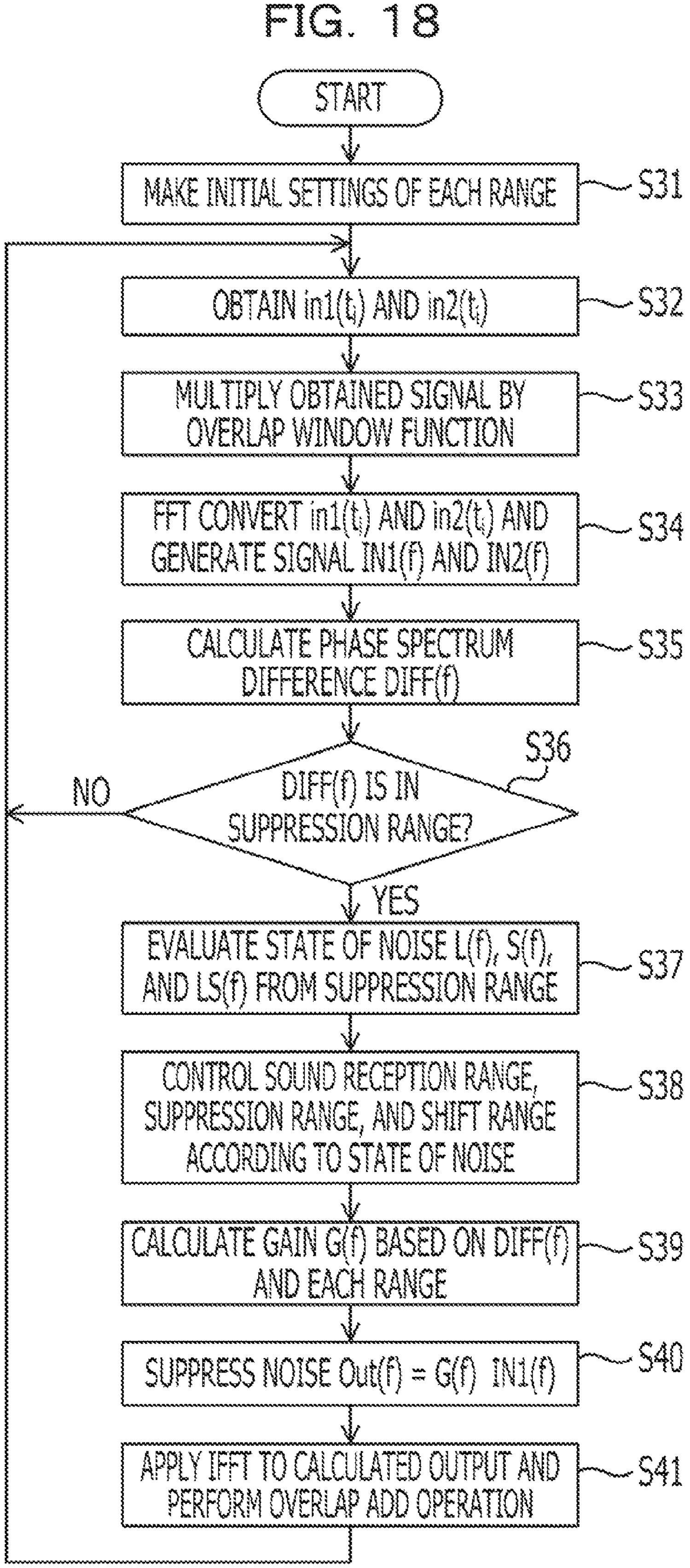
FIG. 18 is a flow chart illustrating noise suppression processing executed by the microphone array device according to the embodiment.

Hereinafter, processing according to the embodiment will be described by referring to FIG. 18. FIG. 18 is one example of a flow chart illustrating noise suppression processing executed by the microphone array device according to the embodiment.

Operation S31 to Operation S38:

The Operation S31 to Operation S38 are substantially the same as the Operation S11 to Operation S18 in FIG. 15 according to the second embodiment. The microphone array device 300 evaluates a state of noise based on sound signals received by the microphone MIC1 and the microphone MIC2 and controls each range based on the state of noise.

Operation S39:

The gain calculation unit 140 calculates a gain G(f) for adjusting a suppression amount of noise on a frequency axis based on the sound reception range, the shift range, and the suppression range that are set based on a state of noise, and the phase spectrum difference DIFF(f).

Operation S40:

The gain multiplication unit 141 multiplies the complex spectrum IN1(*f*) by the gain G(f) to output an OUT(f).

Operation S41:

The signal restoration unit 129 converts the output OUT(f) to a signal on a time axis and further performs an overlap add operation and outputs an output signal in a time domain of the microphone MIC1. After completing the processing, the process returns to Operation S32. The above described processing is repeated at an interval, for example, based on a certain sampling frequency.

As in the first and the second embodiments, noise is suppressed according to the state of noise in the third embodiment as well, and therefore the noise is suppressed according to how much the noise needs to be suppressed. Hence, distortion of a target sound may be suppressed.

Fourth Embodiment

According to the first to the third embodiments, a direction where a target sound source SS is present, in other words, a sound reception direction where the target sound comes is initially set. The microphone array device adjusts a suppression amount of a target sound from the sound reception direction and the sound reception range assuming the sound reception direction as where the target sound comes from. Meanwhile, a microphone array device 400 according to a fourth embodiment detects a direction of a target sound source SS and sets a sound reception direction based on the direction of the target sound source SS. The microphone array device 400 according to the embodiment is applicable to a case when a sound reception direction is initially set, and for example, the initially set sound reception direction is changed, for example, based on the detected direction of the target sound source SS. Hereinafter, the microphone array device 400 according to the fourth embodiment will be described.

The microphone array device 400 according to the fourth embodiment, as in the second and the third embodiments, sound signals obtained by the two microphones MIC1 and MIC2 are processed on a frequency axis. The hardware configuration of the microphone array device 400 according to the fourth embodiment is substantially the same as that of the first embodiment. Moreover, the same reference numerals are assigned to components that are substantially the same as the first embodiment.

(1) Functional Configuration

Figure 19:
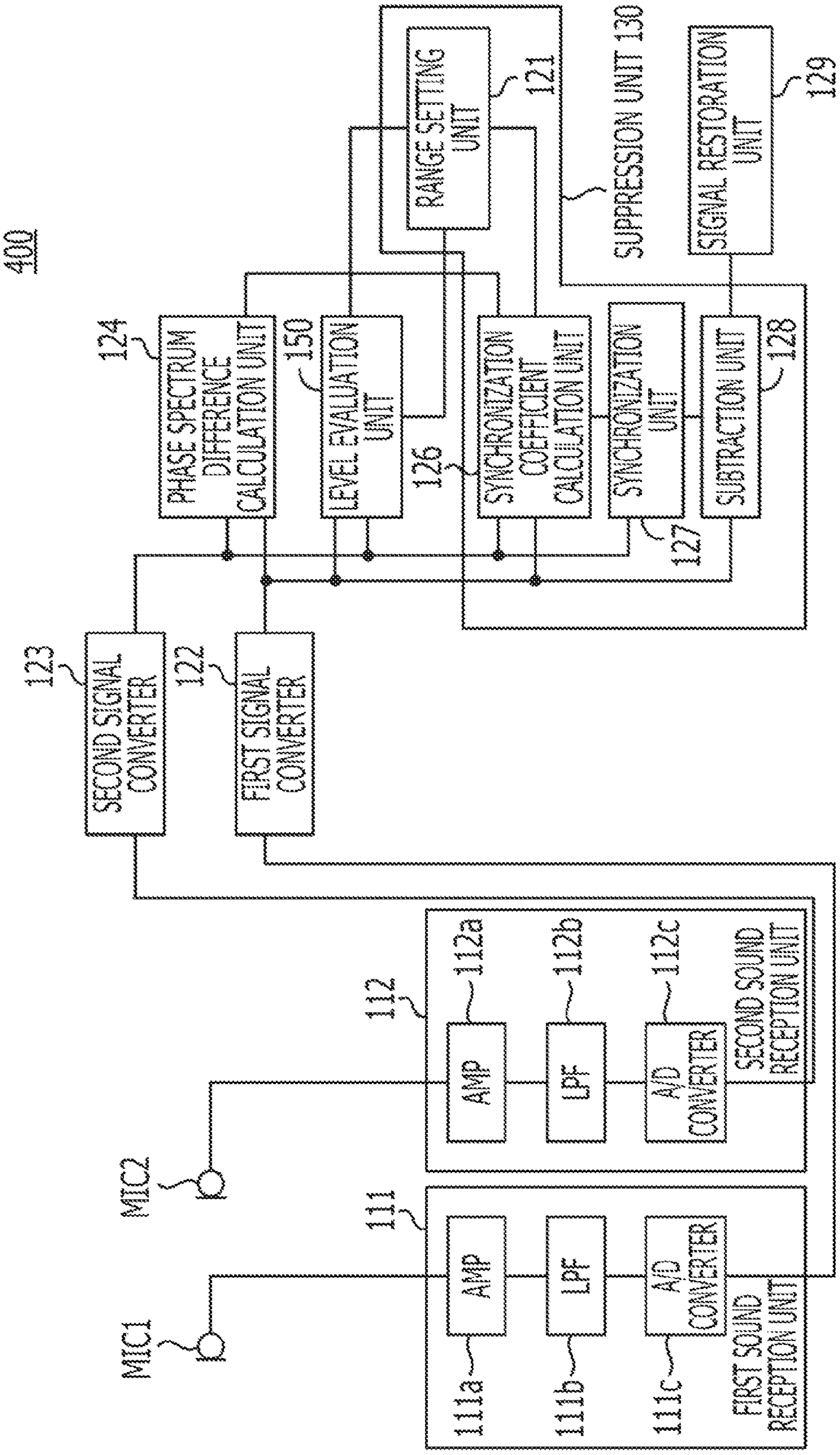
FIG. 19 is a block diagram illustrating a functional configuration of the microphone array device according to a fourth embodiment.

FIG. 19 is one example of a block diagram illustrating a functional configuration of the microphone array device according to the fourth embodiment. The microphone array device 400 according to the fourth embodiment includes a functional configuration that is partially the same as the functional configuration of the microphone array device 200 according to the second embodiment. The microphone array device 400 according to the fourth embodiment includes a first sound reception unit 111, a second sound reception unit 112, a range setting unit 121, a first signal converter 122, a second signal converter 123, a phase spectrum difference calculation unit 124, a synchronization coefficient calculation unit 126, a synchronization unit 127, a subtraction unit 128, and a signal restoration unit 129. The microphone array device 400 in FIG. 19 includes a level evaluation unit 150 instead of the noise state evaluation unit 125 according to the second embodiment. According to the fourth embodiment, a suppression unit 130 includes the range setting unit 121, the synchronization coefficient calculation unit 126, the synchronization unit 127, and the subtraction unit 128.

Hereinafter, a part of the configuration that is different from that of the second embodiment will be described.

(1-1) Range Setting Unit

The range setting unit 121 does not perform initial settings of a sound reception range, a shift range, and a suppression range for each microphone. Accordingly, each of the microphones is set to a state of non-directivity at the initial settings.

Alternatively, the range setting unit 121 may set initial settings of a sound reception range, a shift range, and a suppression range for each microphone based on a user input. Moreover, the range setting unit 121 may set initial settings of the sound reception range, the shift range, and the suppression range for each microphone based on initial values stored in a ROM 102.

Furthermore, the range setting unit 121 receives an evaluation result of a level of a sound received by the two microphones MIC1 and MIC2. The range setting unit 121 controls the sound reception range, the shift range, and the suppression range based on the evaluation result. Controlling the ranges will be described in a paragraph for the level evaluation unit 150 below.

(1-2) Level Evaluation Unit (a) Level Evaluation

The level evaluation unit 150 receives the complex spectrum IN1($f$) and the complex spectrum IN2($f$) from the first signal converter 122 and the second signal converter 123 respectively. The level evaluation unit 150 calculates, for each frequency, a level 1 of a sound signal in1($t_i$) obtained by the microphone MIC1 and a level 2 of a sound signal in2($t_i$) obtained by the microphone MIC2. A level of each sound signal may be calculated by the following expressions (24) and (25).

$$\text{Level }1=\Sigma|\text{IN}1(f)|^2 \quad (24)$$

$$\text{Level }2=\Sigma|\text{IN}2(f)|^2 \quad (25)$$

(b) Detecting a Direction of a Target Sound Source SS

The level evaluation unit 150 detects a magnitude of levels of the above described sound signals and detects a direction of a target sound source SS. For example, the level evaluation unit 150 may detect a direction of a target sound source SS based on an evaluation described below.

The level evaluation unit 150 determines a target sound source SS is present near the microphone MIC1 side when level 1>>level 2. The level 1>>level 2 is, for example, $\Sigma|\text{IN}1(f)|^2 \geq 2.0\times\Sigma|\text{IN}2(f)|^2$.

The level evaluation unit 150 determines a target sound source SS is present at a position where distances to the microphone MIC1 and the microphone MIC2 are substantially the same when level 1≈level 2.

The level evaluation unit 150 determines a target sound source SS is present near the microphone MIC2 side when level 1<<level 2. The level 1<<level 2 is, for example, when $2.0\times\Sigma|\text{IN}1(f)|^2 \leq \Sigma|\text{IN}2(f)|^2$.

The relationship of the level 1, the level 2, and the direction of the target sound source SS may be determined, for example, by an experiment.

The level evaluation unit 150 may determine as described above when the target sound source SS is present, for example, within a distance that is, for example, about 10 times of a microphone distance d from the microphone MIC1 or the microphone MIC2. According to the embodiment, for example, a sound source near the microphone is assumed to be a target sound source SS, for example, a mouth of a user who uses a handset of a telephone.

(c) Controlling Ranges Based on a Direction of a Target Sound Source SS by a Range Setting Unit A method to control the sound reception range, the shift range, and the suppression range based on a direction of the target sound source SS detected by the level evaluation unit 150 will be described.

Figure 20A:
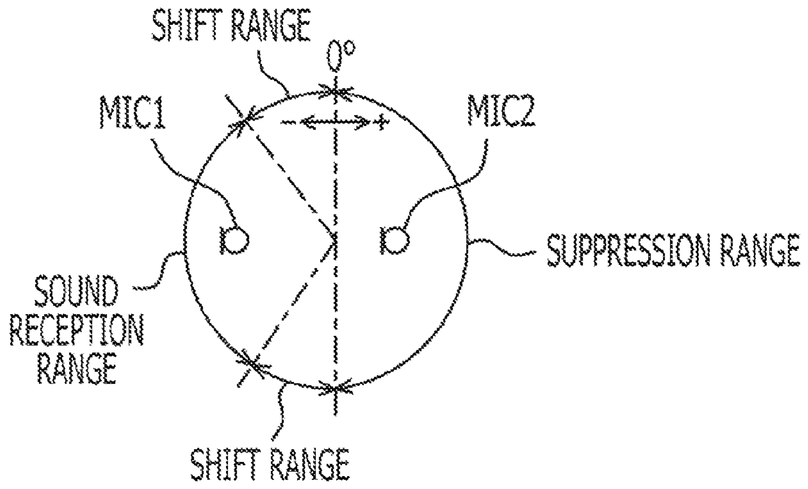
FIG. 20A illustrates one example of a method to control a sound reception range, a shift range, and a suppression range for each microphone when level 1>>level 2.
Figure 20B:
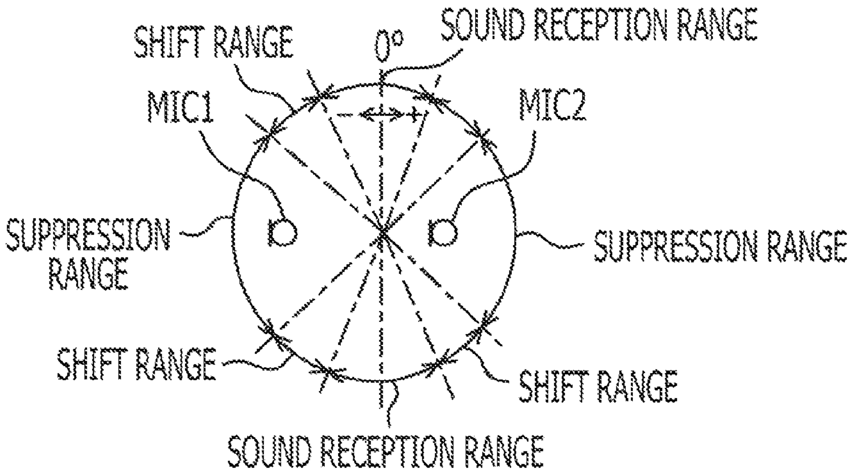
FIG. 20B illustrates one example of a method to control a sound reception range, a shift range, and a suppression range for each microphone when level 1≈level 2.
Figure 20C:
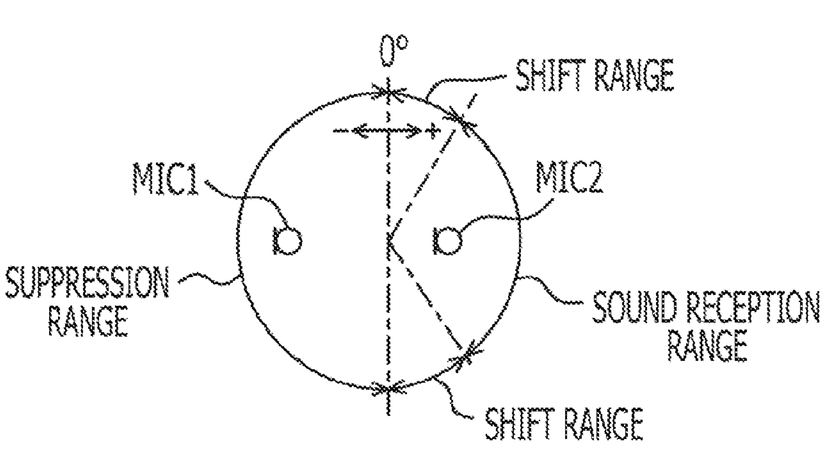
FIG. 20C illustrates one example of a method to control a sound reception range, a shift range, and a suppression range for each microphone when level 1<<level 2.
Figure 21A:
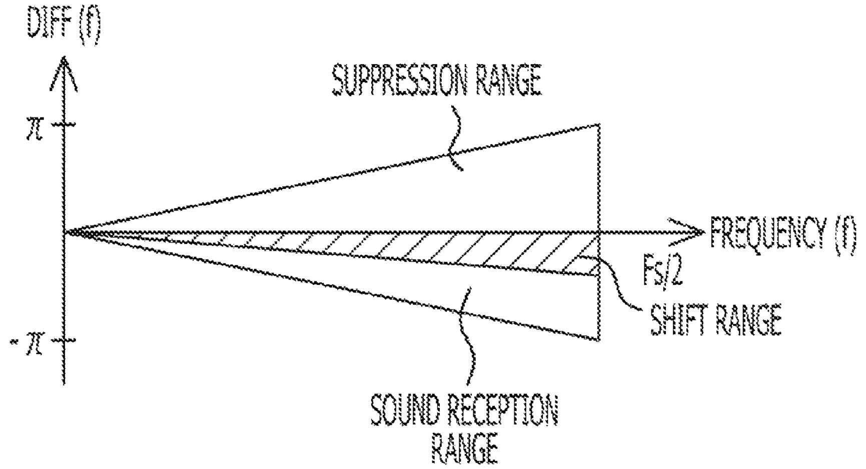
FIG. 21A illustrates a range control of FIG. 20A by a relationship between each frequency and a phase spectrum difference DIFF(f) ($-\pi \leq DIFF(f) \leq \pi$)
Figure 21B:
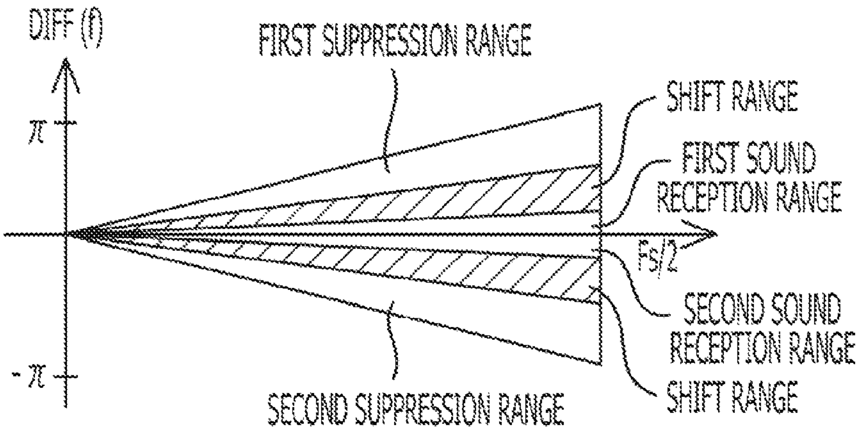
FIG. 21B illustrates a range control of FIG. 20B by a relationship between each frequency and a phase spectrum difference DIFF(f) ($-\pi \leq DIFF(f) \leq \pi$)
Figure 21C:
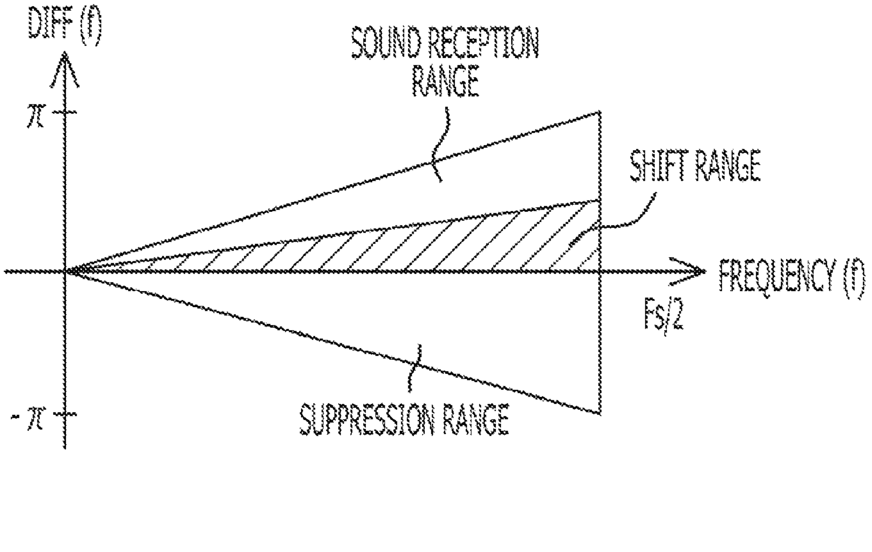
FIG. 21C illustrates a range control of FIG. 20C by a relationship between each frequency and a phase spectrum difference DIFF(f) ($-\pi \leq DIFF(f) \leq \pi$)

FIGS. 20A to 20C are examples of methods to control a sound reception range, a shift range and a suppression range for each microphone. FIGS. 21A to 21C illustrates range control of FIGS. 20A to 20C by a relationship between each frequency and a phase spectrum difference DIFF(f) ($-\pi \leq$DIFF(f)$\leq \pi$).

The range setting unit 121 sets each range, for example, as illustrated in FIGS. 20A and 21A when level 1>>level 2. In other words, the range setting unit 121 sets a sound reception range at the microphone MIC1 side because the target sound source SS is present at the microphone MIC1 side. Meanwhile, the range setting unit 121 sets a suppression range to the microphone MIC2 side and sets a shift range between the sound reception range and the suppression range. In FIG. 20A, the sound reception range and the shift range are set to a minus (MIC1) side from 0 degree, and the suppression range is set to a plus (MIC2) side from 0 degree.

The range setting unit 121 sets the sound reception range narrower than the suppression range because a level 1 of the sound signal in1($t_i$) obtained by the microphone MIC1 is higher than the level 2 of the sound signal in1($t_i$) obtained by the microphone MIC2. The microphone MIC1 may sufficiently receive a target sound from the target sound source SS even if the sound reception range is narrow because the target sound source is estimated to be near the microphone MIC1.

The range setting unit 121 sets each range as illustrated in FIGS. 20B and 21B when level 1≈level 2. In other words, the range setting unit 121 sets a sound reception range in an intermediate point between the microphone MIC1 and the microphone MIC2 because the target sound source SS is present at a position where distances to the microphone MIC1 and the microphone MIC2 are substantially equal. The sound reception range includes a first sound reception range that is an angle range over 0 degree and a second sound reception range that is an angle range under 0 degree. Meanwhile, the range setting unit 121 sets suppression ranges at both sides of the microphone MIC1 and the microphone MIC2. The suppression range includes a first suppression range that is an angle range over $+\pi/2$ and a second suppression range that is an angle range over $-\pi/2$. A range between the sound reception range and the suppression range is set as a shift range. The range setting unit 121 controls so that a volume of the first sound reception range becomes substantially the same volume as the second sound reception range. Moreover, the range setting unit 121 also controls so that a volume of the first suppression range becomes substantially the same volume as the second suppression range. Accordingly, the microphone array device may make suppression amount of noise of each sound signal from the microphone MIC and the microphone MIC2 substantially the same.

The range setting unit 121 sets each range as illustrated in FIGS. 20C and 21C when level 1<<level 2. In other words, the range setting unit 121 sets a sound reception range at the microphone MIC2 side and sets a suppression range at the microphone MIC 1 side because the target sound source SS is present at the microphone MIC2 side. A range between the sound reception range and the suppression range is set as a shift range. In FIG. 20C, the sound reception range and the shift range are set to a plus (MIC2) side from 0 degree, and the suppression range is set to a minus (MIC1) side from 0 degree.

Respective sizes of the sound reception range, the sound suppression range, and the shift range according to a ratio of the level 1 and the level 2 may be determined, for example, by an experiment.

(1-3) Synchronization Coefficient Calculation Unit

The synchronization coefficient calculation unit 126 receives information on the sound reception range, the shift range, and the suppression range that are set based on the level evaluation from the range setting unit 121. The synchronization coefficient calculation unit 126 receives a phase spectrum difference DIFF(f) from the phase spectrum difference calculation unit 124. The synchronization coefficient calculation unit 126 calculates a synchronization coefficient C(f) based on the sound reception range, the shift range, and the suppression range that are set based on the state of noise, and the phase spectrum difference DIFF(f). A method to calculate the synchronization coefficient C(f) is substantially the same as that of the second embodiment. Moreover, the synchronization coefficient calculation unit 126 may calculate a synchronization coefficient Cg(f) that is dependent of a gain g(f) by further multiplying the synchronization coefficient C(f) by the gain g(f) as represented by the expression (20).

(2) Processing Flow

Figure 22:
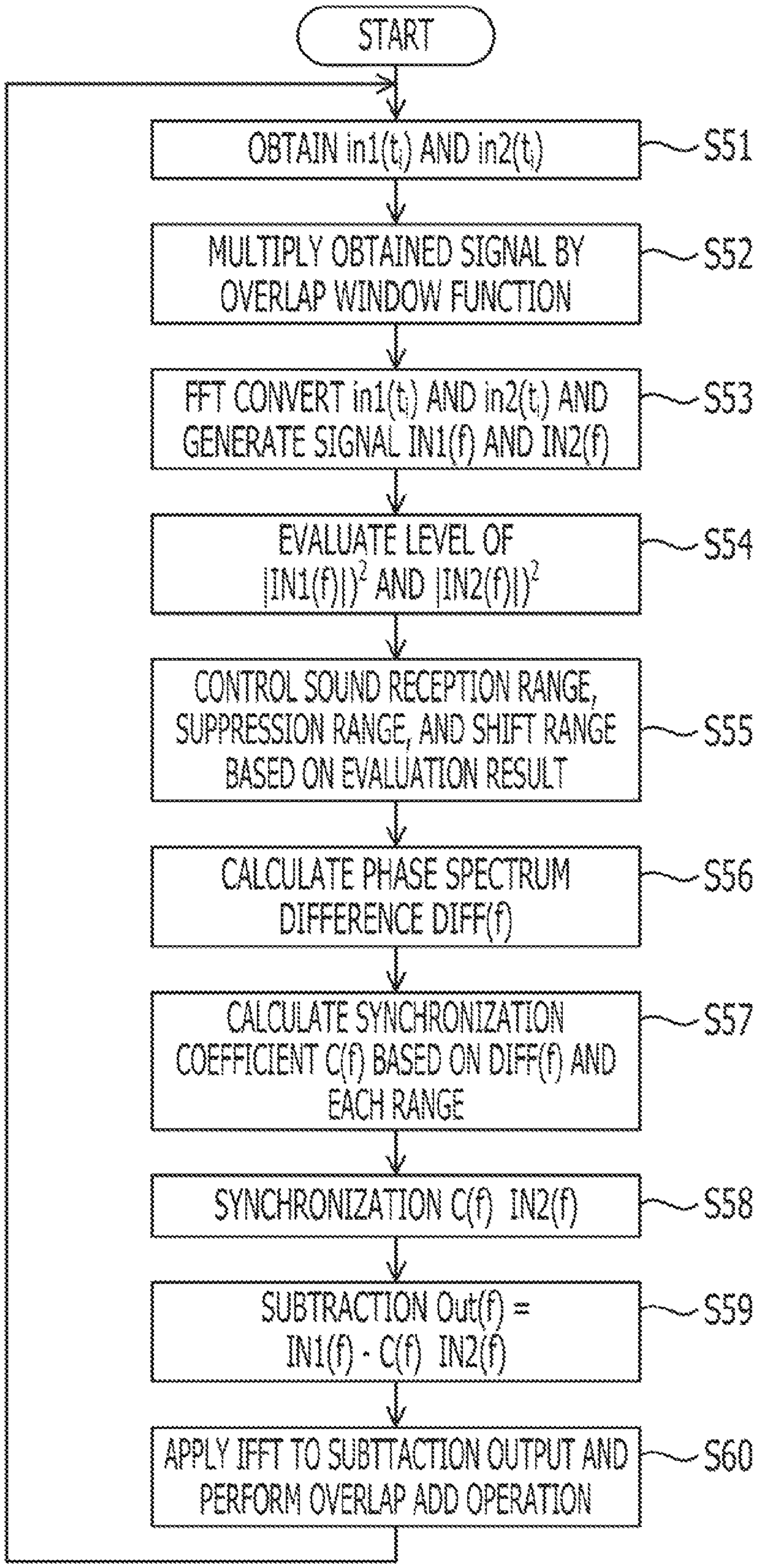
FIG. 22 is one example of a flow chart illustrating range setting processing based on a level ratio executed by the microphone array device according to the embodiment.

Hereinafter, processing according to the embodiment will be described by referring to FIG. 22. FIG. 22 is one example of a flow chart illustrating range setting processing based on a ratio of levels executed by the microphone array device according to the embodiment.

Operation S51 to Operation S53:

Operation S51 to Operation S53 are substantially the same as the Operation S12 to Operation S14 according to the second embodiment. The first sound reception unit 111 and the second sound reception unit 112 obtain a sound signal in1($t_i$) and a sound signal in2($t_i$) on a time axis. The first signal converter 122 generates a complex spectrum IN1($f$) from the sound signal in1($t_i$) on a frequency axis. The second signal converter 123 generates a complex spectrum IN2($f$) from the sound signal in2($t_i$) on the frequency axis.

Operation S54:

The level evaluation unit 150 calculates a level 1 and a level 2 of each sound signal based on the complex spectrum IN1($f$) and the complex spectrum IN2($f$). Moreover, the level evaluation unit 150 identifies a direction of a target sound source SS based on a result of comparison between the level 1 and the level 2.

Operation S55:

The range setting unit 121 controls the sound reception range, the shift range, and the suppression range based on the direction of the target sound source SS.

Operation S56:

The phase spectrum difference calculation unit 124 calculates a phase spectrum difference DIFF(f) between a complex spectrum IN1($f$) and a complex spectrum IN2($f$) for each frequency.

Operation S57 to Operation S60:

Operation S57 to Operation S60 are substantially the same as the Operation S19 to Operation S26 according to the second embodiment. The synchronization coefficient calculation unit 126 calculates the synchronization coefficient C(f) based on the sound reception range, the shift range, and the suppression range that are set based on the level evaluation, and the phase spectrum difference DIFF(f) (Operation S57). Moreover, a synchronization coefficient Cg(f) that is dependent of the gain g(f) may be calculated.

The synchronization unit 127 multiplies the complex spectrum IN2($f$) by the complex spectrum C(f) or the synchronization coefficient Cg(f) to synchronize the complex spectrum IN2($f$) with the complex spectrum IN1 (1) (Operation S58). The subtraction unit 128 subtracts the multiplication result of Operation S58 from the complex spectrum IN1($f$) to obtain an output OUT(f) (Operation S59). The signal restoration unit 129 converts the output OUT(f) from the subtraction unit 128 into a signal on a time axis, further performs an overlap add operation and outputs an output signal in a time domain of the microphone MIC1 (Operation S60). After completing the processing, the process returns to Operation S51 and the above described processing is repeated at an interval, for example, based on a certain sampling frequency.

The microphone array device 400 according to the embodiment sets each range according to a direction of a target sound source SS. For example, an actual direction of a target sound SS may be different from a direction of a target sound source SS that is set beforehand depending on how a mobile phone is held. The microphone array device 400 according to the embodiment may set ranges, for example, a sound reception range according to a change of a direction of the target sound source SS even when the direction of the target source SS is changed. Accordingly, the microphone array device 400 may receive a target sound from the target sound source SS as a sound from the sound reception range, and may suppress noise while suppressing distortion of the target sound.

(3) Combination of the Second Embodiment and the Third Embodiment

The fourth embodiment may be combined with the second embodiment and the third embodiment. In other words, the microphone array device controls the sound reception range, the shift range, and the suppression range based on an evaluation result of a level of sounds received by the two microphones MIC1 and MIC2 as described in the fourth embodiment. The microphone array device controls the sound reception range, the shift range, and the suppression range according to a state of noise as described in the second embodiment and the third embodiment.

(3-1) Combination of the Second Embodiment and the Fourth Embodiment

Figure 23:
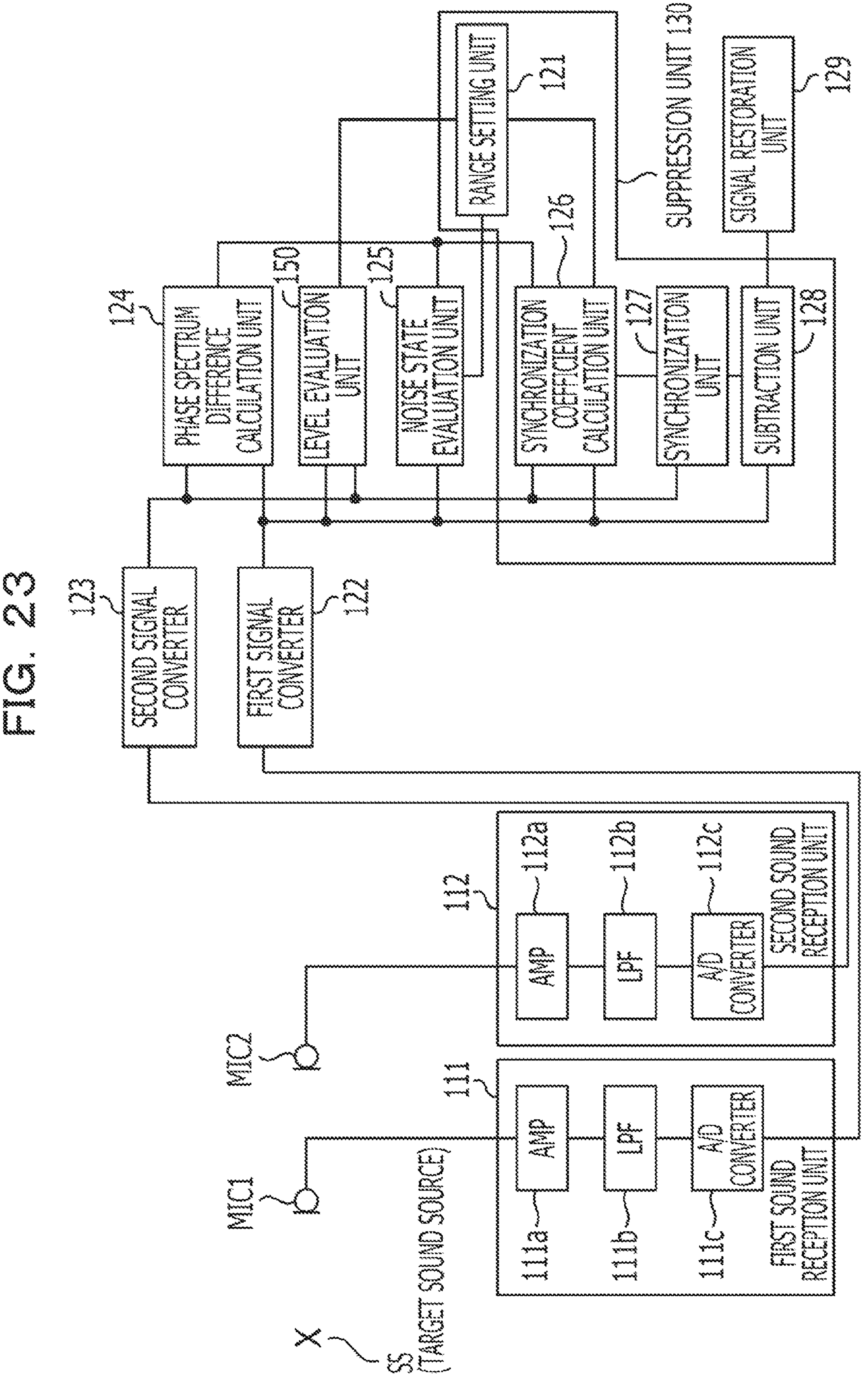
FIG. 23 is one example of a block diagram illustrating a functional configuration when the second embodiment and the fourth embodiment are combined.

FIG. 23 is a block diagram illustrating a functional configuration when the second embodiment and the fourth embodiment are combined. A level evaluation unit 150 is added to the functional configuration in FIG. 6 according to the second embodiment. According to the embodiment, a suppression unit 130 includes a range setting unit 121, a synchronization coefficient calculation unit 126, a synchronization unit 127, and a subtraction unit 128.

The level evaluation unit 150 calculates a level 1 and a level 2 of each sound signal of the microphone MIC1 and the microphone MIC2. Moreover, the level evaluation unit 150 identifies a direction of a target sound source SS by comparing the level 1 and the level 2. The range setting unit 121 controls the sound reception range, the shift range, and the suppression range based on the direction of the target sound source SS. A synchronization coefficient C(f) and so on are calculated based on the range settings, and the signal restoration unit 129 outputs an output signal. The above-described processing to control each range based on the detected direction of the target sound source SS is repeated at an interval, for example, based on a certain sampling frequency.

Meanwhile, the noise state evaluation unit 125 assumes an incoming sound as noise when a phase spectrum difference DIFF(f) is included in the suppression range and evaluates a state of noise as in the second embodiment. The range setting unit 121 obtains a state of noise from the noise state evaluation unit 125 and controls the sound reception range, the shift range, and the suppression range based on the state of noise. Furthermore, a synchronization coefficient C(f) and so on are calculated and the signal restoration unit 129 outputs an output signal. The above described processing to control each range based on the state of noise is repeated at an interval, for example, based on a certain sampling frequency.

Figure 24A:
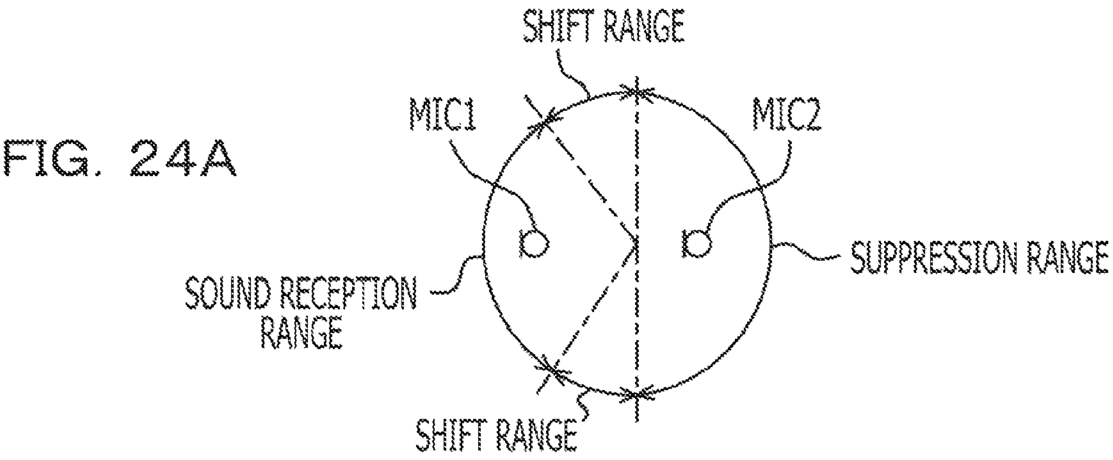
FIG. 24A illustrates one example of a method to set a reception range, a shift range, and a suppression range.
Figure 24B:
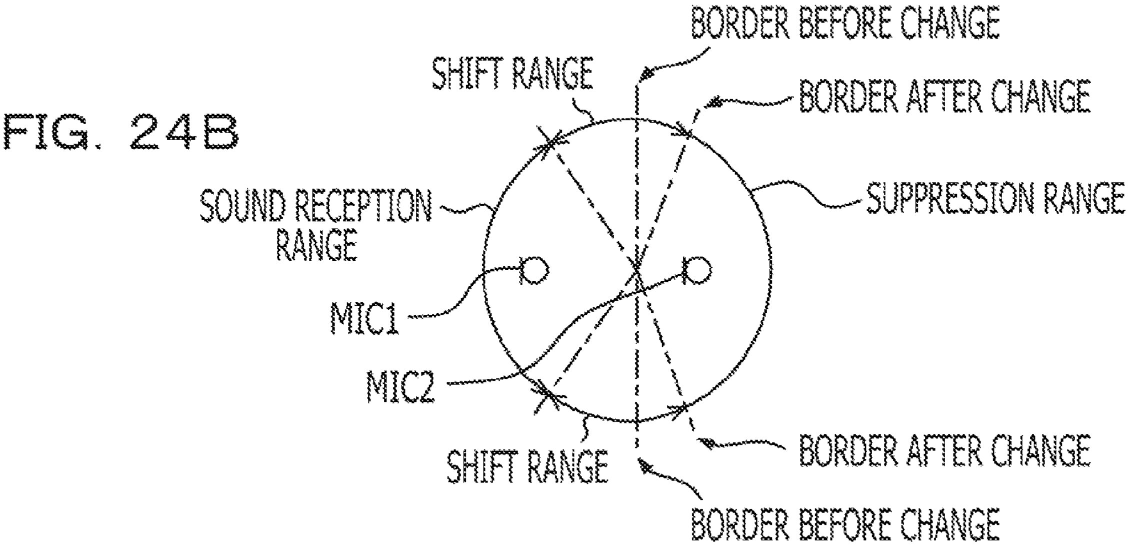
FIG. 24B illustrates one example of a method to control a reception range, a shift range, and a suppression range.
Figure 24C:
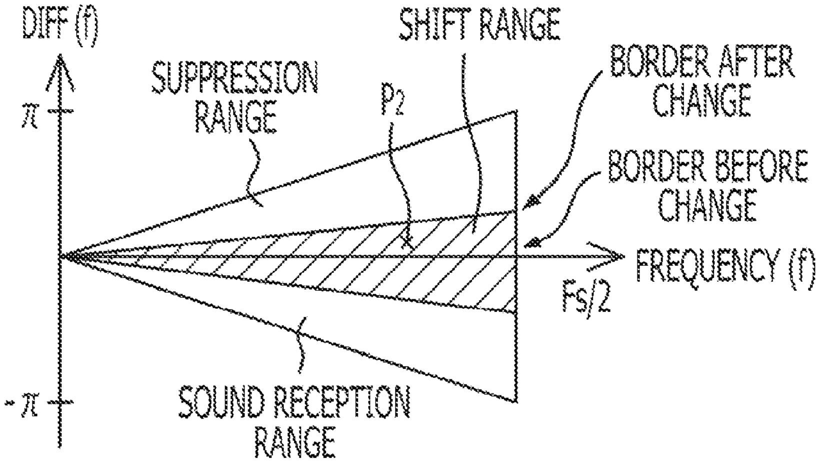
FIG. 24C illustrates a range control of FIG. 24B by a relationship between each frequency and a phase spectrum difference DIFF(f) ($-\pi \leq DIFF(f) \leq \pi$)

An example of controlling ranges will be described by referring to FIGS. 24A to 24C. FIGS. 24A to 24C illustrate one example of a method to control a sound reception range, a shift range, and a suppression range.

For example, as a result of an evaluation by the level evaluation unit 150, levels of sound signals of the microphones MIC1 and MIC2 are assumed to be level 1>>level 2. In this case, the level evaluation unit 150 determines a target sound source SS is present at the microphone MIC1 side. The range setting unit 121 sets a sound reception range at the microphone MIC1 side as illustrated in FIG. 24A and sets a suppression range at the microphone MIC2 side. A range between the sound reception range and the suppression range is set as a shift range.

The noise state evaluation unit 125 assumes an incoming sound as noise when a phase spectrum difference DIFF(f) is included in the suppression range as illustrated in FIG. 24A and evaluates the state of noise. For example, it is assumed as follows: a noise level L(f) is small and the noise level L(f)=0, and a noise level change S(f) is small and the noise level change S(f)=0, and a combined value LS(f)=0. In this case, the range setting unit 121 changes each range as illustrated in FIGS. 24A to 24B. In FIG. 24B, for example, the shift range is expanded and thereby the suppression range is narrowed. A border between the shift range and the suppression range shifts to the suppression range side after the change. Narrowing the suppression range allows to control directivity of the microphone array device so as to suppress noise the sound source of which is in the suppression range while suppressing distortion of a target sound from the target sound source SS in the sound reception range. Moreover, expansion of the shift range allows to shift gradually from the sound reception range to the suppression range, and thereby to gradually change a degree of suppressing noise.

FIG. 24C illustrates a range control of FIG. 24B by a relationship between each frequency and a phase spectrum difference DIFF(f) ($-\pi \leq$DIFF(f)$\leq \pi$). The point P2 is present in the suppression range before expanding the shift range. However, the point P2 is present in the shift range after expanding the shift range. Accordingly, an amount to suppress noise that exhibits characteristics of the point P2 is smaller after changing the shift range than before changing the shift range. Control that expands the shift range while narrowing the suppression range may suppress distortion of a target sound while reducing a suppression amount of noise.

(3-2) Combination of the Third Embodiment and the Fourth Embodiment

Figure 25:
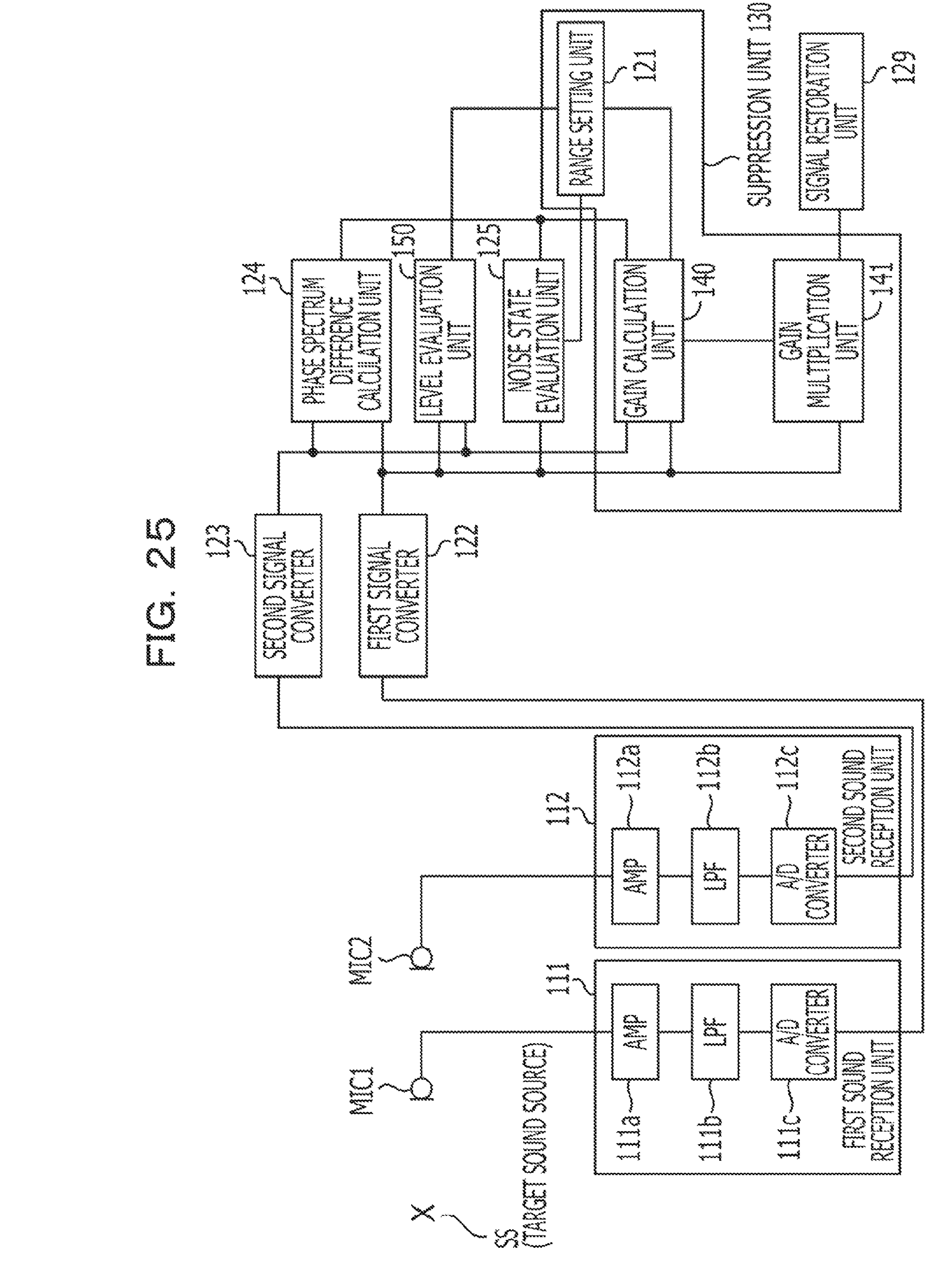
FIG. 25 is one example of a block diagram illustrating a functional configuration when the third embodiment and the fourth embodiment are combined.

FIG. 25 is an example of a block diagram illustrating a functional configuration when the third embodiment and the fourth embodiment are combined. In FIG. 25, a level evaluation unit 150 is further added to the functional configuration in FIG. 16 according to the third embodiment. According to the embodiment that combines the third embodiment and the fourth embodiment, a suppression unit 130 includes a range setting unit 121, a gain calculation unit 140, a synchronization unit 127, and a subtraction unit 128.

The range setting unit 121 controls a sound reception range, a shift range, and a suppression range based on a result of comparison between the level 1 and the level 2 by the level evaluation unit 150.

Meanwhile, the noise state evaluation unit 125 assumes an incoming sound as noise when a phase spectrum difference DIFF(f) is included in the suppression range and evaluates the state of noise as in the second embodiment. The gain calculation unit 140 calculates a gain G(f) for adjusting a suppression amount of noise on a frequency axis based on the sound reception range, the shift range, and the suppression range that are set based on the state of noise, and the phase spectrum difference DIFF(f). The gain multiplication unit 141 multiplies the complex spectrum IN1(*f*) by the gain G(f) to output an OUT(f). The signal restoration unit 129 converts the output OUT(f) into a signal on the time axis and further performs an overlap add operation and outputs an output signal in a time domain of the microphone MIC1. The above-described processing is repeated at an interval, for example, based on a certain sampling frequency As described above, setting each range according to a direction of the target sound source SS and a state of noise may suppress noise while suppressing distortion of the target sound.

Alternative Embodiments

The above described embodiments may be applied to the alternative embodiments described below.

(a) First Alternative Embodiment

The first, second, third, and fourth embodiments use a noise level, a noise level change, and a combined value obtained from the noise level and the noise level change to represent a state of noise. However, the above-described elements that represent a state of noise may be used as a state of noise. Moreover, methods to calculate a noise level, a noise level change, and a combined value are not limited to those described in the first to the fourth embodiments.

(b) Second Alternative Embodiment

The second embodiment and the third embodiment adjust a suppression amount of noise by appropriately taking account of both a noise level L(f) and a noise level change S(f). To this end, the microphone array devices according to the second embodiment and the third embodiment measure duration of a state that noise level L(f)<noise level change S(f) or noise level L(f)>noise level change S(f). The microphone array device adjusts an influence of the noise level L(f) or the noise level change S(f) on the combined value LS(f) according to the duration. In other words, the microphone array device adjusts an influence of noise on a suppression amount of noise.

The adjustment method may be applied to the first embodiment as well. In the first embodiment, the noise level $L(t_i)$ and noise level change $S(t_i)$ are set so that the two values may be compared as in the second embodiment. For example, the noise state evaluation unit 125 calculates a relative value for a full scale for a noise level represented by an average value of $|in\mathbf{1}(t_i)|$. The noise state evaluation unit 125 calculates a noise level $L(t_i)$ based on the relative value. Furthermore, the noise state evaluation unit 125 calculates a ratio of $|in\mathbf{1}(t_i)|$ and the average value of $|in\mathbf{1}(t_i)|$. The noise state evaluation unit 125 calculates a noise level change $S(t_i)$ based on the ratio. As a result, both the noise level $L(t_i)$ and noise level change $S(t_i)$ become 0 or more and 1 or less and may be compared.

(c) Third Alternative Embodiment

The first to the fourth embodiments disclose methods to adjust a suppression amount of noise based on a state of noise and to suppress distortion of a target sound. The configuration to adjust a suppression amount of noise based on the state of noise may be applied, for example, to a synchronous addition method.

(d) Fourth Alternative Embodiment

According to the first to the fourth embodiments, a plurality of microphones is one-dimensionally disposed on a substantially straight line. Among the plurality of microphones, the microphone MIC1 and the microphone MIC2 are used. However, the plurality of microphones may be two-dimensionally disposed, for example, to a vertex of a triangle. Arranging the plurality of microphones two-dimensionally may achieve more complex and finer control of directivity.

(e) Fifth Alternative Embodiment

A microphone array device may be incorporated in devices such as an on-vehicle equipment or a car navigation device with an audio recognition device, a hands-free telephone, or a mobile phone.

(f) Sixth Alternative Embodiment

The above-described processing may be achieved by making each functional unit of the CPU 101 execute programs stored in the ROM 102. However, a signal processing circuit implemented as hardware may execute the above-described processing according to the programs.

(g) Seventh Alternative Embodiment

Moreover, computer programs that make a computer execute the above-described method and a computer readable storage medium that stores the computer programs are included in a scope of the present disclosure. The computer readable storage medium includes, for example, a flexible disk, a hard disk, a Compact Disc-Read Only Memory (CD-ROM), a Magneto Optical (MO) disk, a Digital Versatile Disc (DVD), a DVD-ROM, a DVD-Random Access Memory (RAM), a Blue-ray Disc (BD), a universal serial bus (USB) memory, and a semiconductor memory. The above-described computer programs are not limited to those stored in the storage medium but may be provided through an electric communication line, a wireless or a wired communication lines and a network such as the Internet.

All examples and conditional language recited herein are intended for pedagogical purposes to aid the reader in understanding the principles of the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiments of the present inventions have been described in detail, it should be understood that the various changes, substitutions, and alterations could be made hereto without departing from the spirit and scope of the invention.

What is claimed is:

1. A microphone array device comprising:

a first sound reception circuit component configured to obtain a first sound signal that is input from a first microphone;

a second sound reception circuit component configured to obtain a second sound signal that is input from a second microphone different from the first microphone;

a first signal converter configured to generate first spectra obtained by converting the first sound signal into a frequency component;

a second signal converter configured to generate second spectra obtained by converting the second sound signal into the frequency component;

a phase spectrum difference calculation circuit component configured to calculate a phase spectrum difference between the first spectra and the second spectra for each frequency based on the first spectra and the second spectra;

a noise state evaluation circuit component configured to obtain an evaluation parameter to evaluate an influence of a non-target sound on a target sound based on a spectrum which direction indicated by the phase spectrum difference for the each frequency is included in from a first direction to a second direction among the first spectra; and a suppression circuit component configured to suppress the non-target sound included in the first spectra based on the evaluation parameter.

2. The microphone array device according to claim 1, wherein the noise state evaluation circuit component calculates a level of the spectrum which a direction indicated by the phase spectrum difference for the each frequency is included in from the first direction to the second direction and obtains the evaluation parameter based on the level.

3. The microphone array device according to claim 1, wherein the noise state evaluation circuit component calculates a level change for the spectrum a direction of which indicated by the phase spectrum difference for the each frequency is included in from the first direction to the second direction and obtains the evaluation parameter based on the level change.

4. The microphone array device according to claim 2, wherein the noise state evaluation circuit component further calculates a level change for the spectrum the direction of which indicated by the phase spectrum difference for the each frequency is included in from the first direction to the second direction and obtains the evaluation parameter based on the level change and the level.

5. The microphone array device according to claim 1, the suppression circuit component comprising:

a range setting circuit component configured to change a first suppression range that is from the first direction to the second direction into a second suppression range that is from a third direction to a fourth direction.

6. The microphone array device according to claim 5, wherein the range setting circuit component changes the second suppression range into a wider suppression range as the evaluation parameter becomes larger.

7. The microphone array device according to claim 1, the suppression circuit component comprising:

a synchronization circuit component configured to generate another second spectra that is obtained by synchronizing the second spectra with the first spectra based on the phase spectrum difference calculated for the each frequency and the evaluation parameter; and a subtraction circuit component configured to generate a spectra to be output based on the first spectra and the other second spectra.

* * * * *